(12) United States Patent
Tawbi et al.

(10) Patent No.: US 10,260,108 B2
(45) Date of Patent: Apr. 16, 2019

(54) PARP GENOMIC VARIANTS CONFERRING RESISTANCE AND SENSITIZATION TO CHEMOTHERAPY UNDER INHIBITION

(71) Applicant: University of Pittsburgh—Of the Commonwealth System of Higher Education, Pittsburgh, PA (US)

(72) Inventors: Hussein A. Tawbi, Pittsburgh, PA (US); Petr Pancoska, Pittsburgh, PA (US); Panagiotis Benos, Pittsburgh, PA (US); Marjorie Romkes, San Diego, CA (US); Andrew J. Sedgewick, Brooklyn, NY (US); Irina Abecassis, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 54 days.

(21) Appl. No.: 15/524,242

(22) PCT Filed: Oct. 30, 2015

(86) PCT No.: PCT/US2015/058273
§ 371 (c)(1),
(2) Date: May 3, 2017

(87) PCT Pub. No.: WO2016/073298
PCT Pub. Date: May 12, 2016

(65) Prior Publication Data
US 2017/0342498 A1  Nov. 30, 2017

Related U.S. Application Data

(60) Provisional application No. 62/075,130, filed on Nov. 4, 2014.

(51) Int. Cl.
| | |
|---|---|
| *C12Q 1/68* | (2018.01) |
| *C12Q 1/6886* | (2018.01) |
| *A61K 31/4184* | (2006.01) |
| *A61K 31/495* | (2006.01) |

(52) U.S. Cl.
CPC ........ *C12Q 1/6886* (2013.01); *A61K 31/4184* (2013.01); *A61K 31/495* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 6,316,196 B1* | 11/2001 | Morten | ................ | C12Q 1/6883 435/6.14 |
| 2007/0054278 A1 | 3/2007 | Cargill | | |
| 2012/0035244 A1* | 2/2012 | Chinnaiyan | .......... | A61K 31/501 514/44 A |
| 2014/0038194 A1 | 2/2014 | Wang et al. | | |

FOREIGN PATENT DOCUMENTS

| | | |
|---|---|---|
| WO | WO 2007/130399 A2 | 11/2007 |
| WO | WO 2014/205105 A1 | 12/2014 |

OTHER PUBLICATIONS

Calabrese et al., "Anticancer chemosensitization and radiosensitization by the novel poly (ADP-ribose) polymerase-1 inhibitor AG14361," *Journal of National Cancer Institute* 96: 56-67 (Jan. 7, 2004).
Figueroa et al., "Genetic variation in the base excision repair pathway and bladder cancer risk," *Human Genetics* 121(2): 233-242 (Epub Jan. 3, 2007).
Wang et al., MK-4827, a PARP-1/-2 inhibitor, strongly enhances response of human lung and breast cancer xenografts to radiation, *Investigational New Drugs* 30(6): 2113-2120 (Epub Nov. 30, 2011).
Calabrese et al., "Anticancer chemosensitization and radiosensitization by the novel poly (ADP-ribose) polymerase-1 inhibitor AG14361," *Journal of National Cancer Institute* 96: 56-67 (Jan. 7, 2004)(Abstract only).
Davidson et al., "The PARP inhibitor ABT-888 synergizes irinotecan treatment of colon cancer cell lines" *Investigational New Drugs* (2):461-468 (Epub Oct. 9, 2012).
Davies et al., "Inherited variation in the PARP1 gene and survival from melanoma," *International Journal of Cancer* 135: 1625-1633 (Epub Mar. 6, 2014).
Delaney et al., "Potentiation of temozolomide and topotecan growth inhibition and cytotoxicity by novel poly (adenosine diphosphoribose) polymerase inhibitors in a panel of human tumor cell lines," *Clinical Cancer Research* 6: 2860-2867 (Jul. 2000).
Figueroa et al., "Genetic variation in the base excision repair pathway and bladder cancer risk," *Human Genetics* 121(2): 233-242 (Epub Jan. 3, 2007)(Abstract only).
Fiori et al., Antitumor effect of miR-197 targeting in p53 wild-type lung cancer. *Cell Death and Differentiation* 21(5): 774-82 (Epub Jan. 31, 2014).
International Search Report from parent PCT Application No. PCT/US2015/058273, 6 pages (dated Jan. 4, 2016).
(Continued)

*Primary Examiner* — Jehanne S Sitton
(74) *Attorney, Agent, or Firm* — Klarquist Sparkman, LLP

(57) ABSTRACT

A method is provided for selecting a subject diagnosed with cancer as a candidate for treatment with a PARP1 inhibitor, or both a PARP1 inhibitor and a chemotherapeutic agent such as an alkylating agent. The method includes detecting the presence or absence of a mutation in a non-coding region of a PARP1 gene, wherein the presence of a mutation in the PARP1 gene indicates that the cancer can be treated with the PARP1 inhibitor, optionally in conjunction with the chemotherapeutic agent. In a specific, non-limiting example, the PARP1 inhibitor is veliparib (ABT-888).

17 Claims, 7 Drawing Sheets

Specification includes a Sequence Listing.

(56) References Cited

OTHER PUBLICATIONS

Miknyoczki et al., "Chemopotentiation of temozolomide, irinotecan, and cisplatin activity by CEP-6800, a poly(ADP-ribose) polymerase inhibitor," *Molecular Cancer Therapeutics* 2(4): 371-382 (Apr. 2003).

Ruczinski et al., "A population based study of DNA repair gene variants in relation to non-melanoma skin cancer as a marker of a cancer-prone phenotype," *Carcinogenesis* 33(9): 1692-1698 (Epub May 11, 2012).

Sedgewick et al., "PARP1 variants associated with response to temozolomide in metastatic melanoma patients," *European Journal of Cancer* 49(MC13-0078): S33-34 (Nov. 7-9, 2013).

Tentori et al., "Inhibition of telomerase increases resistance of melanoma cells to temozolomide, but not to temozolomide combined with poly (ADP-Ribose) polymerase inhibitor," *Molecular Pharmacology* 63(1): 192-202 (Jan. 2003).

Wang et al., "Implications of microRNA-197 downregulated expression in esophageal cancer with poor prognosis," *Genetics and Molecular Research* 13(3): 5574-5581 (Jul. 25, 2014).

Wang et al., MK-4827, a PARP-1/-2 inhibitor, strongly enhances response of human lung and breast cancer xenografts to radiation, *Investigational New Drugs* 30(6): 2113-2120 (Epub Nov. 30, 2011)(Abstract only).

Written Opinion from parent PCT Application No. PCT/US2015/058273, 7 pages (dated Jan. 4, 2016).

\* cited by examiner

FIG. 4  PARP1 isoforms and splice variants

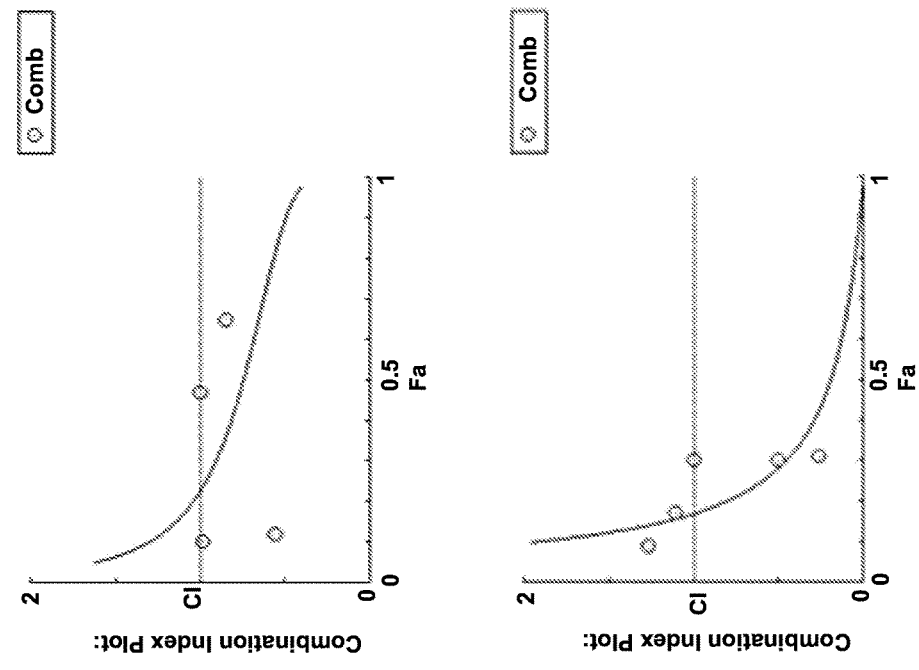
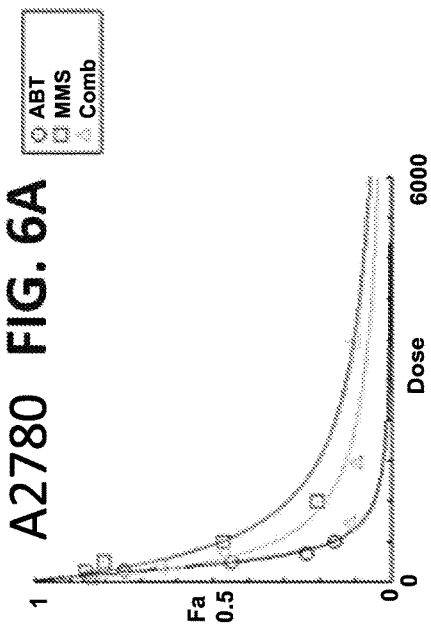
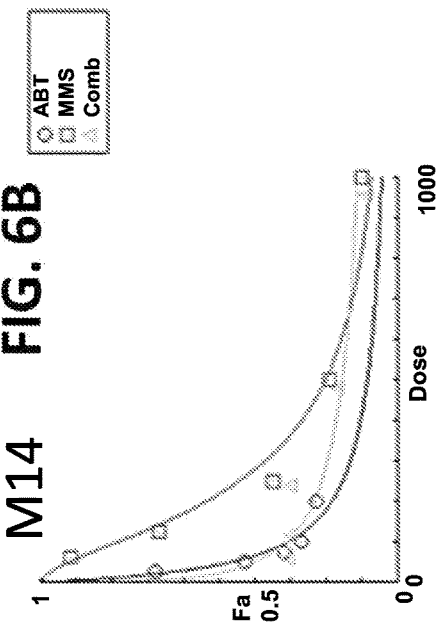

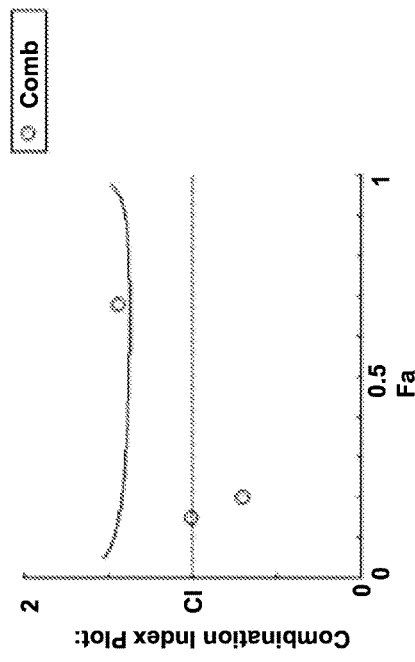
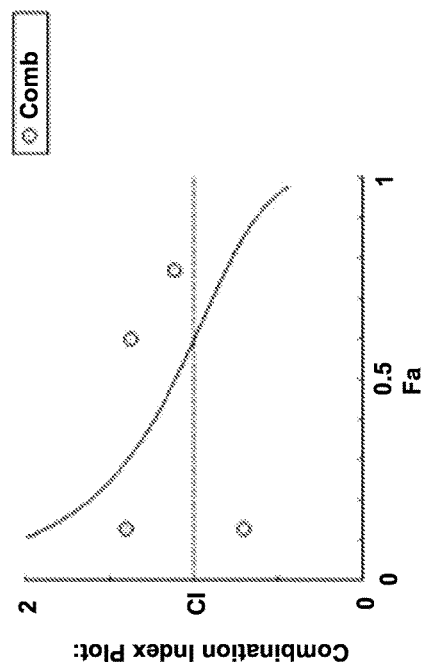
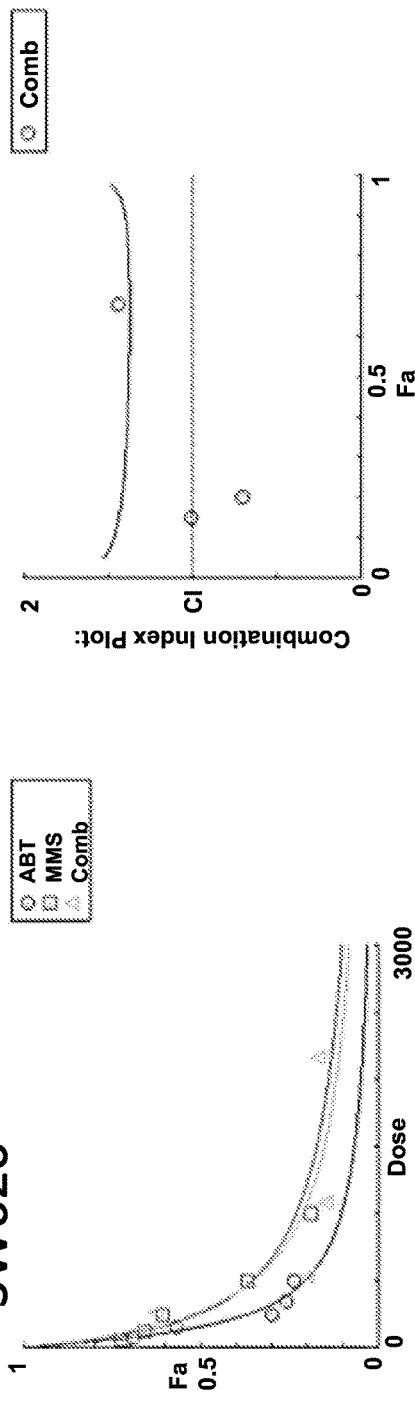
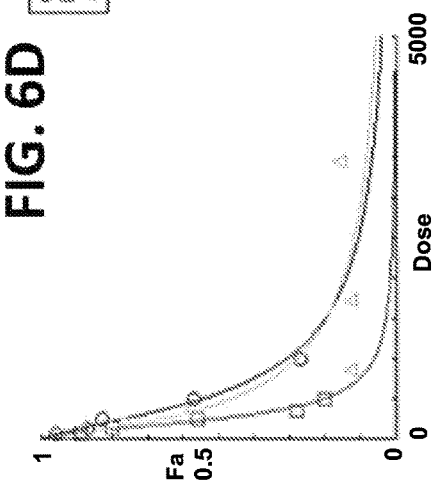
SW620 FIG. 6C
H522 FIG. 6D

PARP GENOMIC VARIANTS CONFERRING RESISTANCE AND SENSITIZATION TO CHEMOTHERAPY UNDER INHIBITION

CROSS REFERENCE TO RELATED APPLICATION

This is a § 371 U.S. national stage of International Application No. PCT/US2015/058273, filed Oct. 30, 2015, which was published in English under PCT Article 21(2), which claims the benefit of U.S. Provisional Application No. 62/075,130, filed Nov. 4, 2014, which is incorporated by reference herein in its entirety.

ACKNOWLEDGMENT OF GOVERNMENT SUPPORT

This invention was made with government support under grant no. T32 EB009403 and grant no. UL1TR000005 awarded by the National Institutes of Health. The government has certain rights in the invention.

FIELD

This disclosure relates to the field of individualized medicine, specifically to the determining if a subject will respond to treatment with a chemotherapeutic agent, such as poly (ADP-ribose) polymerase 1 (PARP1) inhibitor, and optionally a second agent such as an alkylating agent or DNA damaging agent.

BACKGROUND

Cancer is among the leading causes of morbidity and mortality worldwide, with approximately 14 million new cases and 8.2 million cancer related deaths in 2012 (World Cancer Report 2014 and de Martel C, et al. (2012) *Lancet Oncol* 13(6):607-615) and the number of new cases is expected to rise by about 70% over the next 2 decades. Advances in the management of cancers have improved the overall outlook of patients with metastatic malignancies but chemotherapy remains a mainstay of treatment for most common cancers. Virtually all patients develop resistance to chemotherapy after prolonged exposure given the first order kinetics of cytotoxics that generally cannot eradicate cancer. Understanding the mechanisms of this resistance presents new opportunities to improve the therapeutic index of cytotoxic agents and to identify novel drug targets.

Many chemotherapeutic agents function through damaging DNA in tumor cells and therefore the natural DNA repair functions in these cells act against the effect of the chemotherapy. This problem has led to introduction of combination therapies, in which the administration of a chemotherapeutic agent is accompanied by the administration of inhibitor(s) of key molecular components of the DNA repair pathways (Dawar et al., Curr Med Chem. 2012; 19(23):3907-21; ASCO Clin Oncol 27:18s, 2009 (suppl. abstr. 3)). A large proportion of cytotoxic agents exert their effect through DNA damage. Thus, DNA repair pathways represent their most likely mechanisms of resistance and potential drug targets. Base excision repair is the predominant pathway for single strand break (SSB) damage repair utilizing a family of related enzymes termed poly-(ADP-ribose) polymerases (PARP), which are activated by DNA damage (Luo and Kraus W L (2012) *Genes Dev* 26(5):417-432).

Because of its key role in DNA base excision repair, PARP1 is an important target for such inhibitors. PARP inhibitors that are now under investigation in clinical trials include olaparib, niraparib, and BMN 673, all to be tested in upcoming Phase III trials; veliparib (ABT-888) in Phase II trials; rucaparib in Phase I/II development; and CEP-9722 and E7016 in Phase I trials (Fuerst, M. "More Than a Handful of PARP Inhibitors in Development to Treat Hereditary Breast Cancer," Oncology Times 2014, Volume 36(2): 50-51). Olaparib received FDA approval for use in the treatment of platinum-resistant ovarian cancer in 2015. There is evidence (Matthew et al., Mol Cancer Res; 12(8): 1069-1080, 2014: Horton et al., Mol. Cancer Res. 12: 1128-1139, 2014) that because of the multi-factorial nature of the base excision repair process, where PARP1 is a key element, the therapeutic effects and outcomes are sensitive to all changes, modifying the optimal balance in the therapy-carrying pathways and processes. A need remains for methods that identify those subjects with cancer that can be treated with PARP1 inhibitors.

SUMMARY

A method is provided for selecting a subject diagnosed with cancer as a candidate for treatment with a PARP1 inhibitor, or both a PARP1 inhibitor and a chemotherapeutic agent, such as an alkylating agent. The method includes detecting the presence or absence of a mutation in a non-coding region of the PARP1 gene, wherein the presence of a mutation in the PARP1 gene indicates that the cancer can be treated with the PARP1 inhibitor, optionally in conjunction with the chemotherapeutic agent such as an alkylating agent or a DNA damaging agent.

In some embodiments, a method is provided for detecting if a PARP1 inhibitor is effective for treating a cancer in a human subject that includes isolating DNA from a biological sample from the subject and identifying the presence of at least one single nucleotide polymorphism in a non-coding region of a PARP1 gene in the DNA that was isolated from the subject, wherein the presence of the single nucleotide polymorphism in the non-coding region of the PARP1 gene indicates the PARP1 inhibitor, optionally in conjunction with the chemotherapeutic agent such as an alkylating agent or a DNA damaging agent, is effective for treating the cancer in the human subject.

In additional embodiments, a method is provided for detecting if a PARP1 inhibitor is effective for treating a cancer in a human subject that includes performing polymerase chain reaction (PCR) to detect the presence of at least one single nucleotide polymorphism in a non-coding region of a PARP1 gene in a biological sample from the subject, wherein the presence of the single nucleotide polymorphism in the non-coding region of the PARP1 gene indicates the PARP1 inhibitor, optionally in conjunction with the chemotherapeutic agent such as an alkylating agent or a DNA damaging agent, is effective for treating the cancer in the human subject.

In further embodiments, the method includes detecting the presence of the single nucleotide polymorphism by detecting a C at rs1805407 in one or both copies of the PARP1 gene, wherein detection of a C at rs1805407 in one or both copies of the PARP1 gene indicates the PARP1 inhibitor, optionally in conjunction with the chemotherapeutic agent such as an alkylating agent or a DNA damaging agent, is effective for treating the cancer. In other embodiments, detecting the presence of a T at rs1805407 in both copies of the PARP1 gene indicates the PARP1 inhibitor is not effective for treating the subject.

In specific non-limiting examples, the PARP1 inhibitor is olaparib, nirparib, BMN 673, verliparib (ABT-888), rucaparib, CDP-9722, or E7016. Any of the methods disclosed herein can include administering one or more of these inhibitors and/or an alkylating agent to a subject in whom the C has been detected at rs1805407 in one or both copies of the PARP1 gene.

The foregoing and other objects, features, and advantages of the invention will become more apparent from the following detailed description, which proceeds with reference to the accompanying figures.

BRIEF DESCRIPTION OF THE DRAWINGS

FIGS. 6A-6D. Cytotoxic effect of ABT-888, MMS or in combination in mutated vs WT PARP/SNP cell lines. Left panel. Dose-effect curves for MMS, ABT-888 and ABT-888+MMS combination. A2780 (FIG. 6A), M14 (FIG. 6B), SW620 (FIG. 6C) and H522 (FIG. 6D) cells exposed to ABT-888, MMS, or the drug combination (ABT+MMS were combined at the molar ratio of their $IC_{50}$ values in each specific cell line). Right panel. Fraction affected (Fa)-CI plots. Combination index (C.I.) values are plotted as a function of the fractional inhibition (Fa). For each cell line, the mean of three independent experiments is displayed. The Fa-CI plots indicate that the cytotoxic effects of the chemotherapeutic agent MMS is synergistically enhanced by the combination with PARPi (ABT-888) in the mutated PARP1/SNP cell lines, A2780 (FIG. 6A) and M14 (FIG. 6B) (CI<1). In contrast, in the WT PARP/SNP cell lines, SW620 (FIG. 6C) and H522 (FIG. 6D), the interaction between ABT-888 and MMS is antagonistic (CI>1).

SEQUENCE LISTING

Figure 1:
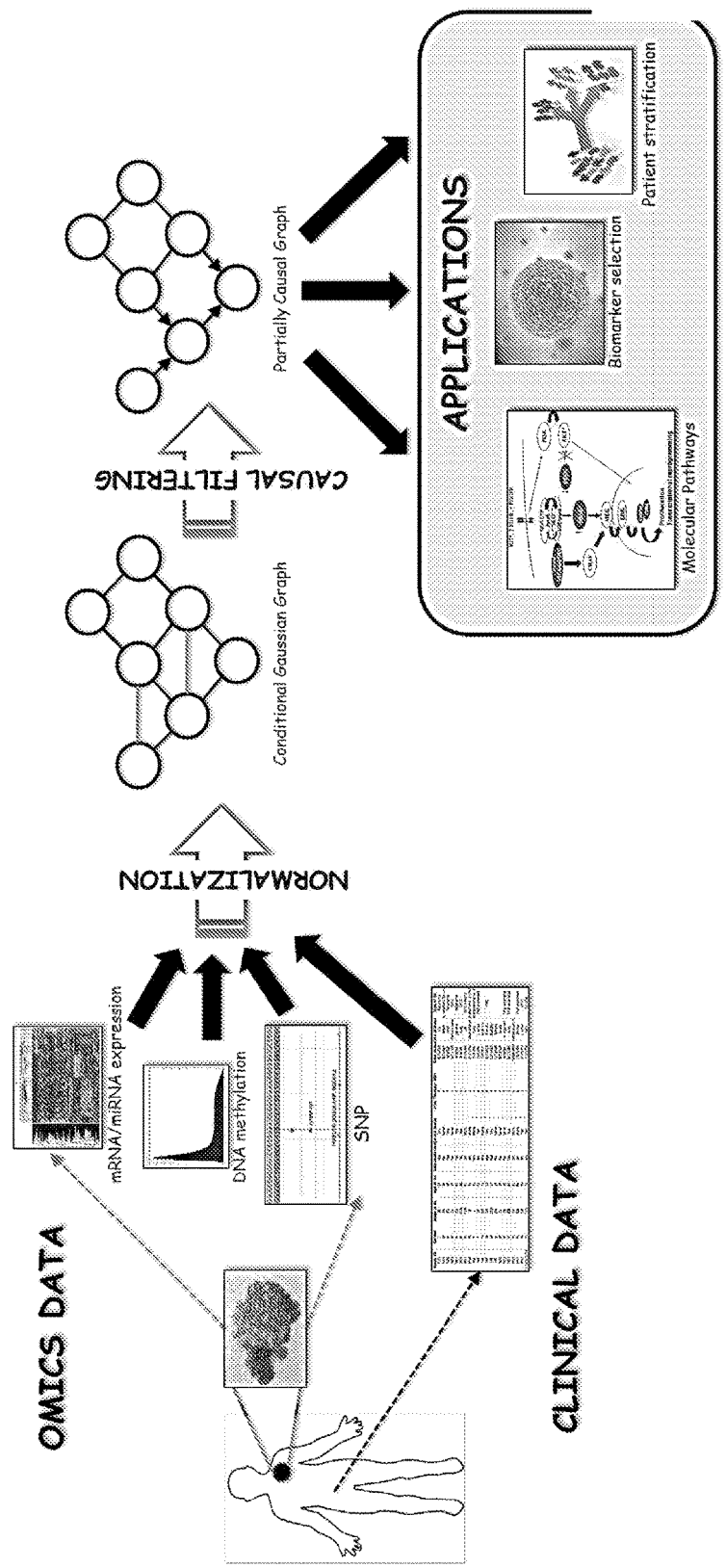
FIG. 1. MGM-Learn workflow implements a generalized network learning strategy over a mixed data types (continuous and discrete variables).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named Sequence Listing, May 3, 2017, 1.09 KB, which is incorporated by reference herein.

DETAILED DESCRIPTION

The present disclosure pertains to genomic-variant mediated resistance or sensitization to chemotherapeutic, DNA repair pathway inhibition and combination treatment (chemotherapy plus DNA repair inhibition) of cancer. An isolated DNA molecule containing the PARP1 gene or its part with locus rs1805407 identified by entromic-powered variant selection or another suitable method within that gene. This locus in the DNA molecule is selected for assay for the presence or absence of specific bases in specific positions for individual patients. In one embodiment/example these bases are T/C nucleotides of rs1805407 in PARP1, in another embodiment these bases are in other SNPs with positions selected by entromic coherence or another suitable method. The SNPs can be used to identify subjects with cancer that will respond to PARP1 inhibitors, optionally in combination with another chemotherapeutic agent such as a DNA damaging agent and/or an alkylating agent.

In some embodiments, a method is provided for identifying compound or compounds that are useful in treating cancer. The method includes providing an assay composition comprising PARP1 gene with variant bases, contacting the assay composition with a test compound and determining the effect of that compound on inhibiting the DNA repair pathway or acting as chemotherapy agent, varied individually or in combination and using the composition of activity assay to quantify the inhibition and chemotherapy effect. In another embodiment, a method is provided for identifying compounds as the second generation DNA repair inhibition and chemotherapy agents and finding the optimal combination of the two, wherein the effects are compared to suitable control identifiers of these compounds that are useful in treating cancer. In some embodiments, the assay composition is a cell extract and in another embodiment the cell culture.

In additional embodiments, a method is provided for identifying a modification of the DNA molecule that is useful in treatment of cancer, such as polymerase chain reaction (PCR) or array-based assay with peripheral blood mononuclear cells, tumor or normal tissue, from patients, or cell lines.

Compositions are also provided that include nucleotide vectors, and methods of inserting these vectors into various cells, thus forming cell lines with wild type and variant bases in the specific loci of PARP1 gene. These nucleotide vectors typically make use of viral particles that are engineered to express the DNA sequence of interest. Cell lines that are transfected with these vectors express the DNA sequence encoding different PARP1 variants, making cells that are wild type to express the variant.

Methods are also provided for evaluation on cell death when the cells have the defined bases in the specific PARP1 gene positions, where the effects are quantified by methods known in the art, such as flow cytometry, spectral viability assays and other methods. An exemplary, non-limiting method for assessment of cell viability is the MTT assay, which is a colorimetric assay. NAD(P)H-dependent cellular oxidoreductase enzymes, under defined conditions, reflect the number of viable cells present. These enzymes are capable of reducing the tetrazolium dye MTT to its insoluble formazan, which has a purple color. Tetrazolium dye assays can also be used to measure cytotoxicity of chemotherapy agents and PAPR inhibitors by measuring the loss of viable cells.

Methods are also provided for evaluating the quantitative measure of response to therapy in vivo (for patients), where the response to therapy after determination of the bases in the selected positions of PARP1 gene are made. These methods preferentially use radiography imaging such as computed tomography (CT) scans. The tumor burden is measured in patients using CT scans and assessed using RECIST criteria to determine the total burden of the disease. Then patients are treated with chemotherapy and/or PARP inhibitors for a number of weeks, then the CT scans are repeated and the total tumor burden is re-assessed. A decrease in the tumor burden by about 30% or more, such as at least about 35%, about 40%, about 45%, about 50%, about 60%, about 65%, about 70%, about 75%, about 80%, about 85%, about 95% or about 100% is considered response to therapy Methods and composition of assays are also provided allowing determination of $IC_{50}$ for efficiency of the drug(s) for the cells and patients with selected PARP1 genetic variants. The $IC_{50}$ or inhibitory concentration-50 is determined using the MTT assay previously described, and is the concentration of an agent (chemotherapy or PARP inhibitor) or a combination at which only 50% of the cells in a culture remain alive. In certain embodiments, the effect (sensitization or resistance) is defined as at a least two-fold increase or decrease of the $IC_{50}$ ratio wait respect to a suitable control.

In additional embodiments, provided is a screening method and composition of assays, comparing the effect to control cells/samples, done in vivo and in vitro and for different cancers, and the exemplary cancer is melanoma. Other embodiments include a screening methodology for the patients. In one embodiment, the source of C/T PARP1 is peripheral blood, where DNA is extracted from peripheral blood mononuclear cells and processed by PCR. Method and composition of the assay identifying the presence of the variant such as sequencing, microarray or another probe based assays with probe composition known for detecting respective PARP1 variants.

The methods and composition of the assays stratify patients to sensitive and resistant to PARP1 inhibition, and sensitive and resistant to combination therapy of PARP inhibitors with chemotherapy, and sensitive and resistant to other cancer treatments. An example is methylation/PARP1 combination therapy for melanoma, ovarian, lung, breast cancers, where patients are identified who will be less sensitive to chemotherapy (antagonism), such that their cancer treatment outcome will be better, if they are not treated with PARP inhibitors compared to being subjected just to chemotherapy alone.

Also provided are a composition and method of identifying the molecules, useful for the development of the second generation drugs, comprising the set of inhibitors of the genes in the DNA base excision repair pathway, preferentially PARP1 and those that are in entromic coherence with PARP1. For PARP1 inhibitors, the in vitro methods use the cells screened/modified to contain only the function-enhancing variants of the PARP1 gene for screening of molecular libraries or inhibitor molecules with new structural modifications designed to improve their biological activity (such as screened by $IC_{50}$, binding constant etc.) as well as their ADMET (absorption, distribution, metabolism, and excretion—toxicity) characteristics by methods known in the art.

The in vivo methods use the patients screened for presence of only the function-enhancing variants of the PARP1 and other genes that are identified.

These methods can be, but are not restricted to, screening molecular libraries, in silico computational methods, including known state of the art graphical model-based methods, entromics-based screening methods, methods used in designing, performing and evaluating clinical trial data.

In additional embodiments, methods are provided for identifying the variations in the molecular structure of the second generation chemotherapeutical agents. These methods use cells screened/modified to contain only the function-enhancing variants and include of only patients carrying the function enhancing variants of said genes into clinical trials. The methods can be, but are not restricted to, screening molecular libraries, in silico computational methods, including known state of the art graphical model-based methods, microRNA screening methods, entromics-based methods etc. using cell lines, genetically modified cells lines with T/C and methods used in designing, performing and evaluating clinical trials.

In yet other embodiments, provided is a composition of molecular tools, vectors and methods for cell modification with the desired genomic types of the relevant genes. In a specific embodiment, this is accomplished by the expression vectors for creating cells with a T/C variant of PARP1 in the locus of rs1805407.

In additional embodiments, a method is provided for testing for resistance and sensitization of chemotherapy for most of cancers, where chemotherapy, targeted therapy, methylation modifying agents or other agents based on modulating base excision repair are administered. Sensitization is measured in cell lines using $IC_{50}$ or in patients using radiographic assessments.

Various kits may be assembled. A kit can contain components to assay for variants in said genes to evaluate a particular patient for the risk of resistance or benefit of sensitization to chemotherapy by DNA repair pathway inhibition and thus allow a clinician to determine whether one, the other or combination treatment for the patient is needed. Such kits can contain reagents that allow variants to be evaluated (primers, reagents, instructions and other components). The primer sequences for PCR based assays included in those kits are provided.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Allele: A particular form of a genetic locus, distinguished from other forms by its particular nucleotide sequence, or one of the alternative polymorphisms found at a polymorphic site.

Allele frequency: A measure of the relative frequency of an allele at a genetic locus in a population. Usually allele frequency is expressed as a proportion or a percentage. In population genetics, allele frequencies are used to depict the amount of genetic diversity at the individual, population, or species level. There are various databases in the public domain that contain SNPs and a user may for example, determine the relative allele frequency in some instances using such publicly available databases.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881); repair chain reaction amplification (see PCT Publication No. WO 90/01069); ligase chain reaction amplification (see European patent publication No. EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134), amongst others.

Array: An arrangement of molecules, such as biological macromolecules (such as polypeptides or nucleic acids) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from a few (such as three) to at least six, at least 20, at least 25, or more. In particular examples, an array includes nucleic acid molecules, such as oligonucleotide sequences that are at least 15 nucleotides in length, such as about 15-40 nucleotides in length, such as at least 18 nucleotides in length, at least 21 nucleotides in length, or even at least 25 nucleotides in length. In one example, the molecule includes oligonucleotides attached to the array via their 5'- or 3'-end.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Breast carcinomas lose the typical histology and architecture of normal breast glands. Generally, carcinoma cells overgrow the normal cells and lose their ability to differentiate into glandular like structures. The degree of loss of differentiation in general is related to the aggressiveness of the tumor. For example, "in situ" carcinoma by definition retains the basement membrane intact, whereas as it progresses to "invasive", the tumor shows breakout of basement membranes. Thus one would not expect to see, within breast carcinomas, staining of a discrete layer of basal cells as seen in normal breast tissue. For a discussion of the physiology and histology of normal breast and breast carcinoma, see Ronnov-Jessen, L., Petersen, O. W. & Bissell, M. J. Cellular changes involved in conversion of normal to malignant breast: importance of the stromal reaction (see, for example, Physiol Rev 76, 69-125, 1996).

Breast cancers can be divided into groups based on their expression profiles. Basal-type carcinomas usually are negative for expression of estrogen receptor (ER) and negative for expression of HER2 (erbB2) and progesterone receptor (PR), and thus are referred to as "triple-negative breast cancers" or "TNBC." This type of breast cancer is also denoted ER$^-$/HER2$^-$/PR$^-$ and represents about 15-20% of all breast cancer, and generally cannot be treated using Her2 targeted or estrogen targeted therapies. It is believed that the aggressive nature of this cancer is correlated with an enrichment for cancer stem cells (CSC) with a CD44$^+$CD24$^{-/lo}$ phenotype. In some embodiments, basal carcinomas are negative for expression of progesterone receptor (PR), positive for expression of epidermal growth factor receptor (EGFR), and positive for expression of cytokeratin 5 (CK5). This phenotype is denoted as follows: ER$^-$/PR$^-$/HER2$^-$/CK5$^+$/EGFR$^+$.

Cancer: A malignant tumor that has undergone characteristic anaplasia with loss of differentiation, increase rate of growth, invasion of surrounding tissue, and is capable of metastasis. For example, thyroid cancer is a malignant tumor that arises in or from thyroid tissue, and breast cancer is a malignant tumor that arises in or from breast tissue (such as a ductal carcinoma). Residual cancer is cancer that remains in a subject after any form of treatment given to the subject to reduce or eradicate the cancer. Metastatic cancer is a tumor at one or more sites in the body other than the site of origin of the original (primary) cancer from which the metastatic cancer is derived. Cancer includes, but is not limited to, solid tumors.

Chemotherapy; chemotherapeutic agents: As used herein, any chemical agent with therapeutic usefulness in the treatment of diseases characterized by abnormal cell growth.

Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

Colon cancer: Colorectal cancer, also called large bowel cancer, includes cancerous growths in the colon, rectum and appendix. With 655,000 deaths worldwide per year, it is the third most common form of cancer and the second leading cause of cancer-related death in the Western world. Many colorectal cancers are thought to arise from adenomatous polyps in the colon. These mushroom-like growths are usually benign, but some may develop into cancer over time. The majority of the time, the diagnosis of localized colon cancer is through colonoscopy. Therapy is usually through surgery, which in many cases is followed by chemotherapy. The first symptoms of colon cancer are usually vague, such as bleeding, weight loss, and fatigue (tiredness). Local (bowel) symptoms are rare until the tumor has grown to a large size. Generally, the nearer the tumor is to the anus, the more bowel symptoms are present.

Concordance: The presence of two or more loci or traits (or combination thereof) derived from the same parental chromosome. The opposite of concordance is discordance, that is, the inheritance of only one (of two or more) parental alleles and/or traits associated with a parental chromosome.

Correlation: A correlation between a phenotypic trait and the presence or absence of a genetic marker (or haplotype or genotype) can be observed by measuring the phenotypic trait and comparing it to data showing the presence or absence of one or more genetic markers. Some correlations are stronger than others, meaning that in some instances subjects with resistance to a PARP1 inhibitor will display a particular genetic marker (i.e., 100% correlation). In other examples the correlation will not be as strong, meaning that a subject with resistance to a PARP1 inhibitor will only display a particular genetic marker 90%, 85%, 70%, 60%, 55%, or 50% of the time. In some instances, a haplotype which contains information relating to the presence or absence of multiple markers can also be correlated to a genetic predisposition such as resistance to a PARP1 inhibitor. Correlations can be described using various statistical analyses known to the skilled artisan.

Decrease: Becoming less or smaller, as in number, amount, size, or intensity. In one example, decreasing the signs and symptoms of cancer includes decreasing tumor volume, tumor size, or metastasis by a desired amount, for example by at least 5%, at least 10%, at least 15%, at least 20%, at least 25%, at least 30%, at least 50%, at least 75%, or even at least 90%, as compared to a response in the absence of a therapeutic composition.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal (termination codon). The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a protein, or a fragment thereof, encompasses both the sense strand and its reverse complement. Thus, for instance, it is appropriate to generate probes or primers from the reverse complement sequence of the disclosed nucleic acid molecules.

Genomic target sequence: A sequence of nucleotides located in a particular region in the human genome that corresponds to one or more specific genetic abnormalities, such as a nucleotide polymorphism, a deletion, an insertion, or an amplification. The target can be for instance a coding sequence; it can also be the non-coding strand that corresponds to a coding sequence. The target can also be a non-coding sequence, such as an intronic sequence. In several examples, genomic target sequences are genomic sequences of genes that encode PARP1

Gene: A segment of DNA that contains the coding sequence for a protein, wherein the segment may include promoters, exons, introns, and other untranslated regions that control expression.

Genotype: An unphased 5' to 3' sequence of nucleotide pair(s) found at a set of one or more polymorphic sites in a locus on a pair of homologous chromosomes in an individual. "Genotyping" is a process for determining a genotype of an individual.

Haplotype: A 5' to 3' sequence of nucleotides found at a set of one or more polymorphic sites in a locus on a single chromosome from a single individual. "Haplotype pair" is the two haplotypes found for a locus in a single individual. With regard to a population, haplotypes are the ordered, linear combination of polymorphisms (e.g., single nucleotide polymorphisms (SNPs) in the sequence of each form of a gene (on individual chromosomes) that exist in the population. "Haplotyping" is a process for determining one or more haplotypes in an individual and includes use of family pedigrees, molecular techniques and/or statistical inference. "Haplotype data" is the information concerning one or more of the following for a specific gene: a listing of the haplotype pairs in an individual or in each individual in a population; a listing of the different haplotypes in a population; frequency of each haplotype in that or other populations, and any known associations between one or more haplotypes and a trait.

Hybridization: Oligonucleotides and their analogs hybridize by hydrogen bonding, which includes Watson-Crick, Hoogsteen or reversed Hoogsteen hydrogen bonding, between complementary bases. Generally, nucleic acids consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to a specific genetic locus, so it specifically hybridizes with a mutant allele (and not the reference allele) or so that it specifically hybridizes with a reference allele (and not the mutant allele).

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization. In one example, an oligonucleotide is specifically hybridizable to DNA or RNA nucleic acid sequences including an allele of a gene, wherein it will not hybridize to nucleic acid sequences containing a polymorphism.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na concentration) of the hybridization buffer will determine the stringency of hybridization, though wash times Also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11.

The following is an exemplary set of hybridization conditions and is not limiting:
Very High Stringency (Detects Sequences that Share at Least 90% Identity)
Hybridization: 5× SSC at 65° C. for 16 hours
Wash twice: 2× SSC at room temperature (RT) for 15 minutes each
Wash twice: 0.5× SSC at 65° C. for 20 minutes each
High Stringency (Detects Sequences that Share at Least 80% Identity)
Hybridization: 5×-6× SSC at 65° C.–70° C. for 16-20 hours
Wash twice: 2× SSC at RT for 5-20 minutes each
Wash twice: 1× SSC at 55° C.–70° C. for 30 minutes each
Low Stringency (Detects Sequences that Share at Least 50% Identity)
Hybridization: 6× SSC at RT to 55° C. for 16-20 hours
Wash at least twice: 2×-3× SSC at RT to 55° C. for 20-30 minutes each.

Isolated: An "isolated" biological component (such as a nucleic acid molecule, protein or organelle) has been substantially separated or purified away from other biological components in the cell of the organism in which the component naturally occurs, i.e., other chromosomal and extrachromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Linkage: The association of two or more loci at positions on the same chromosome, such that recombination between the two loci is reduced to a proportion significantly less than 50%. The term linkage can also be used in reference to the association between one or more loci and a trait if an allele (or alleles) and the trait, or absence thereof, are observed together in significantly greater than 50% of occurrences. A linkage group is a set of loci, in which all members are linked either directly or indirectly to all other members of the set.

Locus: A location on a chromosome or DNA molecule corresponding to a gene or a physical or phenotypic feature, where physical features include polymorphic sites.

Melanoma: A form of cancer that originates in melanocytes (cells that make the pigment melanin). Melanocytes are found primarily in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism) which is a marker of aggressive behavior and a tendency to local recurrence. Other melanomas include clear cell sarcoma, mucosal melanoma, and uveal melanoma.

Features that affect prognosis are tumor thickness in millimeters (Breslow's depth), depth related to skin structures (Clark level), type of melanoma, presence of ulceration, presence of lymphatic/perineural invasion, presence of tumor infiltrating lymphocytes (if present, prognosis is better), location of lesion, presence of satellite lesions, and presence of regional or distant metastasis.

Mutation: Any change of a nucleic acid sequence as a source of genetic variation. For example, mutations can occur within a gene or chromosome, including specific changes in non-coding regions of a chromosome, for instance changes in or near regulatory regions of genes. Types of mutations include, but are not limited to, base substitution point mutations (which are either transitions or transversions), deletions, and insertions. Missense mutations are those that introduce a different amino acid into the sequence of the encoded protein; nonsense mutations are those that introduce a new stop codon; and silent mutations are those that introduce the same amino acid often with a base change in the third position of the codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

Non-coding: A change in nucleotide sequence that does not result in the production of a codon that encodes for an amino acid other than the wild-type human sequence, and therefore does not result in the production of any alteration in polypeptide sequence. In the instant application, the term "non-coding" refers to the exclusion of non-synonymous SNPs or haplotypes. In addition, the term "non-coding" also excludes promoter regions of a gene and is therefore limited to intronic and exonic domains of the gene.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

In several examples, oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 70 bases, for example about 10-25 bases, such as 12, 15 or 20 bases.

Poly (ADP-Ribose) Polymerase 1 (PARP1): An enzyme that modifies nuclear proteins by ADP-ribosylation. The modification is dependent on DNA and is involved in the regulation of cellular processes such as differentiation, proliferation, and tumor transformation. PARP1 also plays a role in the regulation of the molecular events involved in the recovery of cell from DNA damage. An exemplary PARP1 nucleic acid sequence is disclosed in GENBANK® Accession No. NM_001618.3, May 18, 2014, incorporated herein by reference. An exemplary PARP1 protein sequence is disclosed in GENBANK® Accession No. NP_001609.2, incorporated herein by reference. A PARP inhibitor is an agent that significantly decreases the activity of the PARP1 enzyme as measured with decreased PARylation of different proteins, most commonly PARP1 protein itself. Detection of inhibition of PARylation can be detected using Western Blot or other assays such as ELISA.

Phased: As applied to a sequence of nucleotide pairs for two or more polymorphic sites in a locus, phased means the combination of nucleotides present at those polymorphic sites on a copy of the DNA for the locus.

Polymorphism: A variation in a gene sequence. The polymorphisms can be those variations (DNA sequence differences) which are generally found between individuals or different ethnic groups and geographic locations which, while having a different sequence, produce functionally equivalent gene products. Typically, the term can also refer to variants in the sequence which can lead to gene products that are not functionally equivalent. Polymorphisms also encompass variations which can be classified as alleles and/or mutations which can produce gene products which may have an altered function. Polymorphisms also encompass variations which can be classified as alleles and/or mutations which either produce no gene product or an inactive gene product or an active gene product produced at an abnormal rate or in an inappropriate tissue or in response to an inappropriate stimulus. Alleles are the alternate forms that occur at the polymorphism.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation.

In the instant application "polymorphism" refers a traditional definition, in that the definition "polymorphism" means that the minor allele frequency must be greater than at least 1%.

Preventing, treating or ameliorating a disease: "Preventing" a disease (such as a cancer) refers to inhibiting the full development of a disease, such as cancer. "Treating" refers to a therapeutic intervention that ameliorates a sign or symptom of a disease or pathological condition after it has begun to develop. "Ameliorating" refers to the reduction in the number or severity of signs or symptoms of a disease.

Probes and primers: A probe comprises an isolated nucleic acid capable of hybridizing to a target nucleic acid. A detectable label or reporter molecule can be attached to a probe or primer. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 15 nucleotides in length, such as at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, or more contiguous nucleotides complementary to the target nucleic acid molecule, such as 20-70 nucleotides, 20-60 nucleotides, 20-50 nucleotides, 20-40 nucleotides, or 20-30 nucleotides.

Primers are short nucleic acid molecules, for instance DNA oligonucleotides are 10 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 55, 60, 65, 70 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, or more contiguous nucleotides complementary to the target nucleic acid molecule to be amplified, such as a primer of 15-70 nucleotides, 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein. It is also appropriate to generate probes and primers based on fragments or portions of these disclosed nucleic acid molecules, for instance regions that encompass the identified polymorphisms of interest. PCR primer pairs can be derived from a known sequence by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Reference Allele or Wild-type: A genotype that predominates in a natural population of organisms that do not have a disease process, or that have normal sensitivity to a certain chemotherapeutic agent, such as a PARP1 inhibitor. The reference genotype differs from mutant forms.

Sample: A sample, such as a biological sample, is a sample obtained from a subject. As used herein, biological samples include all clinical samples useful for detection of renal disease in subjects, including, but not limited to, cells, tissues, and bodily fluids, such as: blood; derivatives and fractions of blood, such as serum; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes blood obtained from a human subject, such as whole blood or serum.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to −1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2.

To compare two amino acid sequences, the options of Bl2seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, at least 70%, at least 80%, at least 90%, at least 95%, at least 98%, or at least 99% sequence identity determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid. One of skill in the art will appreciate that the particular sequence identity ranges are provided for guidance only.

Single nucleotide polymorphism (SNP): A single base (nucleotide) polymorphism in a DNA sequence among individuals in a population. Typically in the literature, a single nucleotide polymorphism (SNP) may fall within coding sequences of genes, non-coding regions of genes, or in the intergenic regions between genes (e.g., introns). SNPs within a coding sequence will not necessarily change the amino acid sequence of the protein that is produced, due to degeneracy of the genetic code. A SNP in which both forms lead to the same polypeptide sequence is termed "synonymous" (sometimes called a silent mutation)—if a different polypeptide sequence is produced they are "nonsynonymous". A nonsynonymous change may either be missense or "nonsense", where a missense change results in a different amino acid, while a nonsense change results in a premature stop codon. In some examples, a SNP can be in the non-coding sequence of a gene.

Subject: Living multi-cellular vertebrate organisms, a category that includes human and non-human mammals (such as laboratory or veterinary subjects).

Therapeutic agent: A chemical compound, small molecule, or other composition, such as an antisense compound, antibody, peptide, nucleic acid molecule, protease inhibitor, hormone, chemokine or cytokine, capable of inducing a desired therapeutic or prophylactic effect when properly administered to a subject. For example, therapeutic agents for melanoma include agents that prevent or inhibit development or metastasis of melanoma.

Therapeutically effective amount: An amount of a therapeutic agent, such as a PARP1 inhibitor, that alone, or together with one or more additional therapeutic agents, induces the desired response, such as reduction of tumor burden, reduction of tumor volume and/or a decrease in metastasis. Ideally, a therapeutically effective amount provides a therapeutic effect without causing a substantial cytotoxic effect in the subject. The preparations disclosed herein are administered in therapeutically effective amounts. A therapeutically effective amount of a composition can be determined by varying the dosage of the product and measuring the resulting therapeutic response. The therapeutically effective amount can be dependent on the source applied, the subject being treated, the severity and type of the condition being treated, and the manner of administration.

Tumor, neoplasia, malignancy or cancer: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma and CNS tumors (such as a glioma, astrocytoma, medulloblastoma, craniopharyrgioma, ependymoma, pinealoma, hemangioblastoma, acoustic neuroma, oligodendroglioma, meningioma, neuroblastoma and retinoblastoma).

Unless explained otherwise, all technical and scientific terms used herein have the same meaning as commonly understood to one of ordinary skill in the art to which this disclosure belongs. In case of conflict, the present specification, including explanations of terms, will control. Explanation of common terms and methods in pharmacology may be found in *Remington's Pharmaceutical Sciences*, by E.W. Martin, Mack Publishing Co., Easton, Pa., 15th Edition, 1975 and *Goodman & Gilman's The Pharmacological Basis of Therapeutics*, by L. Brunton et al., The McGraw Hill Companies, Inc., Twelfth Edition (2011).

All publications, patent applications, patents, GEN-BANK® Accession numbers and other references mentioned herein are incorporated by reference in their entirety. In case of conflict, the present specification, including explanations of terms, will control. In addition, the materials, methods, and examples are illustrative only and not intended to be limiting.

The singular forms "a," "an," and "the" refer to one or more than one, unless the context clearly dictates otherwise. For example, the term "comprising a specimen" includes single or plural specimens and is considered equivalent to the phrase "comprising at least one specimen." The term "or" refers to a single element of stated alternative elements or a combination of two or more elements, unless the context Methods for Identifying Subjects A method is provided for determining if a subject diagnosed with cancer as a candidate for treatment with a PARP1 inhibitor, or both a PARP1 inhibitor and a chemotherapeutic agent, such as an alkylating agent and/or a DNA damaging agent. The method includes detecting the presence or absence of a mutation in a non-coding region of the PARP1 gene, wherein the presence of a mutation in the PARP1 gene indicates that the cancer can be treated with the PARP1 inhibitor, optionally in conjunction with the chemotherapeutic agent.

In some embodiments, a method is provided for detecting if a PARP1 inhibitor is effective for treating a cancer in a human subject that includes isolating DNA from a biological sample from the subject and identifying the presence of at least one single nucleotide polymorphism in a non-coding region of a PARP1 gene in the DNA that was isolated from the subject, wherein the presence of the single nucleotide polymorphism in the non-coding region of the PARP1 gene indicates the PARP1 inhibitor is effective for treating the cancer in the human subject. In additional embodiments, a method is provided for detecting if a poly (ADP-ribose) polymerase (PARP)1 inhibitor, optionally in combination with a second chemotherapeutic agent, is effective for treating a cancer in a human subject. The method includes performing polymerase chain reaction (PCR) or using an array to detect the presence of at least one single nucleotide polymorphism in a non-coding region of a PARP1 gene in a biological sample from the subject. The presence of the single nucleotide polymorphism in the non-coding region of the PARP1 gene indicates the PARP1 inhibitor, optionally in combination with a second chemotherapeutic agent, is effective for treating the cancer in the human subject. The second chemotherapeutic agent can be an alkylating agent and/or a DNA damaging agent.

In some embodiments, the method includes detecting the presence of the single nucleotide polymorphism comprises detecting a C at rs1805407 in one or both copies of a PARP1 gene, wherein detection of a C at rs1805407 in one or both copies of the PARP1 gene indicates the PARP1 inhibitor is effective for treating the cancer alone or in combination with chemotherapy. In other embodiments, detecting the presence of a T at rs1805407 in both copies of the PARP1 gene indicates the PARP1 inhibitor is not effective for treating the subject and may even be antagonistic to chemotherapy. In some embodiments, the methods include obtaining a sample including nucleic acids from a human subject of interest, and analyzing the sample for the presence of the SNP in these nucleic acids. The cancer can be any cancer of interest, including, but not limited to, melanoma, ovarian cancer, lung cancer, colon cancer or breast cancer. The chemotherapy can include an alkylating agent and/or a DNA damaging agent.

The sample can be any sample of interest. Biological samples include all clinical samples useful for detection of renal disease in subjects, such as cells, tissues, and bodily fluids, for example blood; derivatives and fractions of blood, such as polymorphonuclear cells; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes blood obtained from a human subject, such as whole blood or isolated blood cells. The sample can be a tissue biopsy or cancer cells. In another particular example, a sample includes buccal cells, for example collected using a swab or by an oral rinse. In additional embodiments, the method includes analyzing DNA sequence data previously obtained from the subject of interest. In further embodiments, the sample comprises tumor cells. The sample can be any sample that incudes genomic DNA.

Thus, the methods can include selecting a subject with cancer, and obtaining a sample including nucleic acids from this subject. For example, the subject can have a melanoma, an ovarian cancer, a lung cancer, a colon cancer, a breast cancer, or any other cancer for which chemotherapeutic agents are utilized. The presence of a tumor can be determined by methods known in the art, and typically include cytological, pathological, radiographic, and morphological evaluation.

Generally, the methods utilize the detection of one or more SNPs in a non-coding region in the PARP1 gene. In several embodiments, the methods include detecting the presence of more than one SNP. In some embodiments, the method include detecting a C at rs1805407 in one or both copies of the PARP1 gene, wherein detection of a C at rs1805407 in one or both copies of the PARP1 gene indicates the PARP1 inhibitor, optionally combined with another chemotherapeutic agent, is effective for treating the cancer. The additional chemotherapeutic agent can be an alkylating agent or DNA damaging agent.

With regard to a SNPs, the SNPs can be identified by name. The exact sequence of the SNP can be determined from the database of SNPs available at the NCBI website (Entrez SNP, dbSNP build 128, Jan. 28, 2009). The "position" of the nucleotide of interest is the location in the genome of the SNP, referring to the nucleotide position from the p-terminus of the chromosome in the human genome, see the NCBI SNP website, available on the internet. Sequence information for rs1805407 is:

```
WILD-TYPE ALLELE
                                       (SEQ ID NO: 1)
TGGGAGAGGGCAAGCTGGGGGAGGTTTGCTTTGCTCTCTGAGACGAGGC
CC

VARIANT ALLELE
                                       (SEQ ID NO: 2)
TGGGAGAGGGCAAGCTGGGGGAGGTCTGCTTTGCTCTCTGAGACGAGGC
CC
```

The complement is:

```
WILD-TYPE ALLELE
                                       (SEQ ID NO: 3)
ACCCTCTCCCGTTCGACCCCCTCCAAACGAAACGAGAGACTCTGCTCCG
GG

VARIANT ALLELE
                                       (SEQ ID NO: 4)
ACCCTCTCCCGTTCGACCCCCTCCAGACGAAACGAGAGACTCTGCTCCG
GG
```

The sequence at dbSNP contains the reverse-complement (SEQ ID NOs: 3 and 4) of the referenced sequence (SEQ ID NOs: 1 and 2, respectively). See: the worldwide web at ncbi_nlm_nih_gov/projects/SNP/snp_ref.cgi?rs=1805407, as available on Nov. 1, 2014. This sequence is incorporated herein by reference. The chromosomal location of the SNP rs1805407 in GRCh38 is Chr1:226,402,132.

Single nucleotide polymorphisms are identified in the leading strand. Due to the complementary nature of DNA, the single nucleotide polymorphism is present in both DNA strands, and thus can also be identified in the lagging strand. Due to the nature of the genetic code, the detection of a C at rs1805407 in a variant PARP1 gene intrinsically detects a G in the complement of the rs1805407 in a variant P PARP1 gene. Similarly, detecting a G in the complement of rs1805407 in a variant PARP1 gene intrinsically detects a C in rs1805407 in a variant PARP1 gene. In addition, to the nature of the genetic code, the detection of a T at rs1805407 in a wild-type PARP1 gene intrinsically detects an A in the complement of the rs1805407 in a wild-type P PARP1 gene. Similarly, detecting an A in the complement of rs1805407 in a wild-type PARP1 gene intrinsically detects a T in rs1805407 in a wild-type PARP1 gene. Thus, any of the methods disclosed herein intrinsically encompass detection of the complement of in either a wild-type or variant of rs1805407. All of the methods disclosed herein, and the claims, inherently encompass detection of the corresponding nucleotide in the complement.

The presence of detection of a C at rs1805407 in one or both copies of the PARP1 gene indicates the PARP1 inhibitor, optionally combined with another chemotherapeutic agent, is effective for treating the cancer. The detection of a T rs1805407 in both copies of the PARP1 gene indicates the PARP1 inhibitor, optionally combined with another chemotherapeutic agent is not effective for treating the cancer.

The PARP1 inhibitor can be any compound of interest. In some embodiments, the PARP1 inhibitor is a 4-carboxamido-isoindolinone derivative, see Published U.S. Patent Application No. 2015/0274662, incorporated herein by reference. Additional PARP1 inhibitors are 4-hydroxyquinazoline and its derivatives, Carboxamino-benzimidazole and its derivatives, 4-aminonaphtalimide and its derivatives, PJ34 homologues, and tetracycline derivatives (see Published U.S. Patent Application No. 2011/0098255, incorporated herein by reference). Additional PARP1 inhibitors are tetraaza phenalen-3-one compounds, see Published U.S. Patent Application No. 2009/0098084, incorporated herein by reference. An exemplary PARP1 inhibitors are 4-iodo-3-nitrobenzamide. The synthesis of BA (4-iodo-3-nitrobenzamide) is described in U.S. Pat. No. 5,464,871, which is incorporated herein by reference.

In some embodiments, the PARP1 inhibitor is

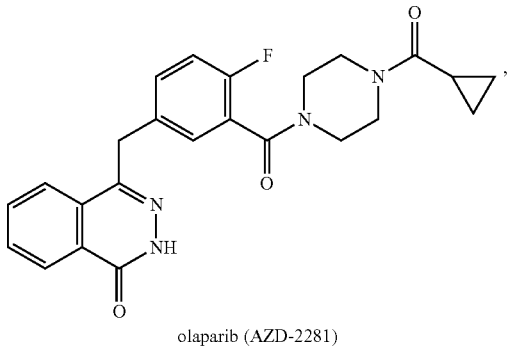

olaparib (AZD-2281)

-continued

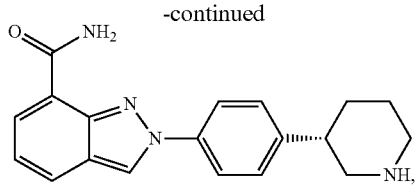

niraparib (MK-4827)

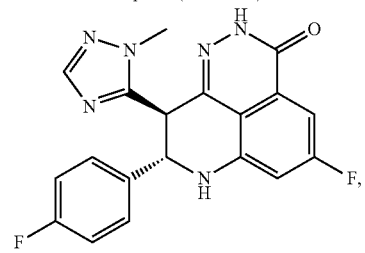

BMN 673

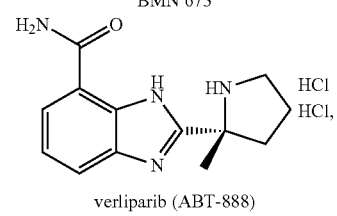

veliparib (ABT-888)

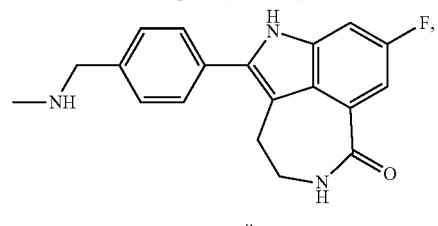

rucaparib

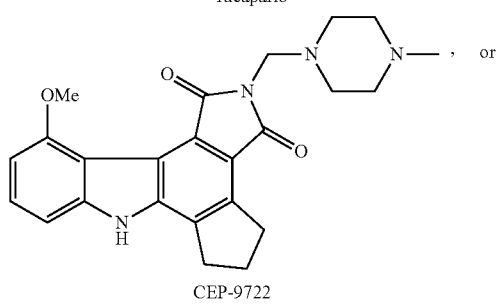

CEP-9722

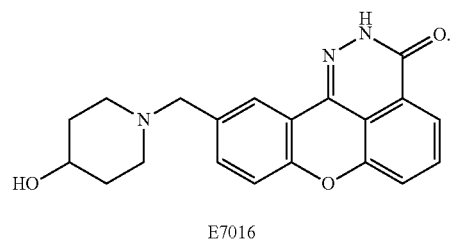

E7016

In some non-limiting examples, the PARP1 inhibitor reduces activity by at least 90% in a cell with a wild-type PARP1 gene.

In some embodiments, the PARP1 inhibitor is used alone. In additional embodiments, it is used in combination with another chemotherapeutic agent. Clinical development of PARP1 inhibitors follows two distinct approaches: A. targeting cells that are genetically predisposed to die when PARP1 activity is lost; and B. combining PARP1 inhibition with DNA-damaging agents (M Rouleau, A Patel, M J Hendzel, S H Kaufmann, PARP1 and beyond, Nature Reviews (2010) 10, 293-301 (April 2010).

Examples of chemotherapeutic agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Specific non-limiting examples of alkylating agents are temozolomide and dacarbazine. Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech). In a specific non-limiting example the chemotherapeutic agent is TMZ.

In some embodiments, the method further comprises administering to the subject a therapeutically effective amount of the PARP1 inhibitor. PARP1 inhibitors are disclosed above. In some examples, the PARP1 inhibitor is aparib, nirparib, BMN 673, verliparib (ABT-888), rucaparib, CDP-9722, or E7016. In additional embodiments, the method further comprises administering to the subject the PARP1 inhibitor in combination with an additional chemotherapeutic agent, such as a DNA damaging agent or an alkylating agent. In one example, this administration is sequential. In other examples, this administration is simultaneous. Suitable chemotherapeutic agents are disclosed above. In a specific, non-limiting example, and alkylating agent is administered to the subject, such as, but not limited to, Temozolomide or dacarbazine. Additional non-limting examples are carmustine, cyclophosphamide and parthenolide. Any of the alkylating agent or DNA damaging agent disclosed herein can be utilized.

Treatment of the conditions described herein are generally initiated after the development of a condition described herein, or after the initiation of a precursor condition (such as dysplasia or development of a benign tumor). Treatment can be initiated at the early stages of cancer, for instance, can be initiated before a subject manifests symptoms of a condition, such as during a stage I diagnosis or at the time dysplasia is diagnosed. However, treatment can be initiated during any stage of the disease, such as but not limited to stage I, stage II, stage III and stage IV cancers.

Treatment initiated after the development of a condition, such as malignant cancer, may result in decreasing the severity of the symptoms of one of the conditions, or completely removing the symptoms, or reducing metastasis, tumor volume or number of tumors. Treatment can also include increasing the immune response to the tumor, such as by increasing the humoral response. In one example, there is an increase in antibodies that specifically bind the tumor. In some examples, treatment is administered to these subjects with a benign tumor that can convert into a malignant or even metastatic lesion. However, in other examples, treatment is administered to any subject diagnosed with cancer. Exemplary tumors are lymphomas, cervical carcinoma, prostate cancers, breast cancers, colon cancers or lung cancers.

In one aspect of the disclosure, the formation of tumors, such as metastasis, are delayed, prevented or decreased. In another aspect, the size of the primary tumor is decreased. In a further aspect, a symptom of the tumor is decreased. In yet another aspect, tumor volume is decreased.

The quantitative measure of response to therapy can be evaluated in vivo. These methods can include the use of radiography imaging such as computed tomography (CT) scans. The tumor burden can be measured in patients using CT scans and assessed using RECIST criteria to determine the total burden of the disease. The subject is are treated with a PARP inhibitor and optionally a chemotherapeutic agent such as a DNA damaging agent or the alkylating agent, then the CT scans are repeated and the total tumor burden is re-assessed. In some embodiments, decrease in the tumor burden by about 30% or more, such as at least about 35%, about 40%, about 45%, about 50%, about 60%, about 65%, about 70%, about 75%, about 80%, about 85%, about 95% or about 100% is considered response to therapy Methods of detecting mutations in a gene are well known in the art. Detection of one or more mutations in the PARP1 gene can be accomplished using any suitable technique, such as those described in detail in the sections below. For example, PARP1-specific primers can be used to amplify PARP1 nucleic acid from a biological sample (such as a tumor tissue sample or blood sample). The amplified molecule can then be sequenced and compared to a reference PARP1sequence (such as SEQ ID NO: 1), or compared with PARP1 from a control sample such as a non-cancerous tissue sample, to detect a mutation in PARP1. PARP1 amplification primers and sequencing primers can be designed according to well-known methods. Mutations in PARP1 can also be detected using oligonucleotides that specifically hybridize with a particular mutation. Hybridization of such oligonucleotides can be detected by labeling the oligonucleotide with a detectable marker, such as a fluorescent marker, enzymatic marker or radioisotope.

For detection of PARP1 mutations, nucleic acid can be isolated from a biological sample according to well-known methods. In some embodiments, the biological sample is tissue sample, such as a tumor tissue sample. In other embodiments, the biological sample is a fluid sample, such as blood. For example, nucleic acid can be isolated from cells obtained from a blood sample. In some embodiments, the biological sample is obtained from a patient diagnosed with melanoma, ovarian cancer, lung cancer, colon cancer or breast cancer.

Methods of Detecting Single Nucleotide Polymorphisms (SNPs)

The methods disclosed herein utilize the detection of one or more SNPs in a non-coding region in the PARP1 gene. In several embodiments, the methods include detecting the presence of more than one SNP. In some embodiments, the methods include detecting a C at rs1805407 in one or both copies of the PARP1 gene. In specific non-limiting examples, detection of a C at rs1805407 in one of both copies of the PARP1 gene indicates the PARP1 inhibitor, optionally combined with another chemotherapeutic agent, is effective for treating cancer. The additional chemotherapeutic agent can be an alkylating agent.

Detecting a single nucleotide polymorphism (SNP) in a non-coding region of the PARP1 gene can be accomplished using any technique known in the art. For example, the presence or absence of an SNP can be determined by conventional methods such as DNA sequencing, oligonucleotide hybridization, polymerase chain reaction (PCR) amplification with primers specific to the mutation, Generally, the nucleic acid sequence of the PARP1 gene can be detected by any suitable method or technique of detecting gene sequence. Such methods include, but are not limited to, PCR, reverse transcriptase-PCR (RT-PCR), in situ PCR, in situ hybridization, Southern blot, sequence analysis, microarray analysis, or other hybridization platforms.

Nucleic acid molecules can be prepared for analysis using any technique known to those skilled in the art. Generally, such techniques result in the production of a nucleic acid molecule sufficiently pure to determine the presence or absence of one or more variations at one or more locations in the nucleic acid molecule. Such techniques are described for example, in Sambrook, et al., Molecular Cloning: A Laboratory Manual (Cold Spring Harbor Laboratory, New York) (1989), and Ausubel, et al., Current Protocols in Molecular Biology (John Wiley and Sons, New York) (1997), incorporated herein by reference.

When the nucleic acid of interest is present in a cell, it can be necessary to first prepare an extract of the cell and then perform further steps, such as differential precipitation, column chromatography, extraction with organic solvents and the like, in order to obtain a sufficiently pure preparation of nucleic acid. Extracts can be prepared using standard techniques in the art, for example, by chemical or mechanical lysis of the cell. Extracts then can be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. When chaotropic salts are used, it can be desirable to remove the salts from the nucleic acid-containing sample. This can be accomplished using standard techniques in the art such as precipitation, filtration, size exclusion chromatography and the like.

Detection of point mutations in target nucleic acids can be accomplished by molecular cloning of the target nucleic acid molecules and sequencing the nucleic acid molecules using techniques well known in the art. Alternatively, amplification techniques such as PCR can be used to amplify target nucleic acid sequences directly from a genomic DNA preparation from a tumor tissue or cell sample. The nucleic acid sequence of the amplified molecules can then be determined to identify mutations. The design and selection of appropriate primers is well within the abilities of one of ordinary skill in the art.

Increased use of polymerase chain reaction (PCR) methods has stimulated the development of many programs to aid in the design or selection of oligonucleotides used as primers for PCR. Four examples of such programs that are freely available via the Internet are: PRIMER™ by Mark Daly and Steve Lincoln of the Whitehead Institute (UNIX, VMS, DOS, and Macintosh), Oligonucleotide Selection Program by Phil Green and LaDeana Hiller of Washington University in St. Louis (UNIX, VMS, DOS, and Macintosh), PGEN™ by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Designing oligonucleotides for use as either sequencing or PCR primers to detect requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding programs. If a possible stem structure is observed, the sequence of the primer can be shifted a few nucleotides in either direction to minimize the predicted secondary structure. When the amplified sequence is intended for subsequence cloning, the sequence of the oligonucleotide can also be compared with the sequences of both strands of the appropriate vector and insert DNA. A sequencing primer only has a single match to the target DNA. It is also advisable to exclude primers that have only a single mismatch with an undesired target DNA sequence. For PCR primers used to amplify genomic DNA, the primer sequence can be compared to the sequences in the GENBANK™ database to determine if any significant matches occur. If the oligonucleotide sequence is present in any known DNA sequence or, more importantly, in any known repetitive elements, the primer sequence should be changed.

PARP1 primer pairs can be used for determination of the nucleotide sequence of a target nucleic acid using nucleic acid amplification techniques such as the polymerase chain reaction. The pairs of single stranded DNA primers can be annealed to sequences within or surrounding the target nucleic acid sequence in order to prime amplification of the target sequence.

Allele-specific PCR differentiates between target regions differing in the presence of absence of a variation or polymorphism. PCR amplification primers are chosen based upon their complementarity to the target sequence, such as nucleic acid sequence in a haplotype block including a SNP, a specified region of an allele including a SNP, or to the SNP itself. The primers bind only to certain alleles of the target sequence. This method is described by Gibbs, *Nucleic Acid Res.* 17:12427 2448, 1989. Further screening methods employ the allele-specific oligonucleotide (ASO) screening methods (e.g. see Saiki et al., *Nature* 324:163-166, 1986). Oligonucleotides with one or more base pair mismatches are generated for any particular allele. ASO screening methods detect mismatches between one allele in the target genomic or PCR amplified DNA and the other allele, showing decreased binding of the oligonucleotide relative to the second allele (i.e. the other allele) oligonucleotide. Oligonucleotide probes can be designed that under low stringency will bind to both polymorphic forms of the allele, but which at high stringency, only bind to the allele to which they correspond. Alternatively, stringency conditions can be devised in which an essentially binary response is obtained, i.e., an ASO corresponding to a variant form of the target gene will hybridize to that allele (haplotype block), and not to the reference allele (haplotype block).

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_M$). Melting domains are at least 20 base pairs in length, and can be up to several hundred base pairs in length.

The ligase chain reaction (Wu et al., *Genomics* 4:560-569, 1989) and allele-specific PCR (Ruano and Kidd, *Nucleic Acids Res.* 17:8392, 1989) can also be used to amplify target nucleic acid sequences. Amplification by allele-specific PCR uses primers that hybridize at their 3' ends to a particular target nucleic acid mutation. If the particular mutation is not present, an amplification product is not observed. Amplification Refractory Mutation System can also be used to detect mutations in nucleic acid sequences (U.S. Pat. No. 5,595,890; Newton et al., *Nucleic Acids Res.* 17:2503-2516, 1989). Insertions and deletions of genes can also be detected by cloning, sequencing and amplification. In addition, restriction fragment length polymorphism probes for the gene or surrounding marker genes can be used to score alteration of an allele or an insertion in a polymorphic fragment. Single stranded conformation polymorphism analysis can also be used to detect base change variants of an allele (Orita et al., *Proc. Natl. Acad. Sci. USA* 86:2766-2770, 1989). Other known techniques for detecting insertions and deletions can also be used with the claimed methods.

In a similar manner, DNA probes can be used to detect mismatches, for example through enzymatic or chemical cleavage (Cotton et al., *Proc. Natl. Acad. Sci. USA* 85: 4397-4401, 1988; Shenk et al., *Proc. Natl. Acad. Sci. USA* 72:989-993, 1975). Alternatively, mismatches can be detected by shifts in the electrophoretic mobility of mismatched duplexes relative to matched duplexes (Cariello, *Am. J. Hum. Genet.* 42:726-734, 1988). With DNA probes, the target nucleic DNA which may contain a mutation can be amplified before hybridization. Changes in target nucleic acid DNA can also be detected using hybridization methods.

Amplified nucleic acid sequences can also be screened using allele-specific probes. These probes are nucleic acid oligomers, each of which contains a region of the target nucleic acid gene harboring a known mutation. For example, one oligomer may be about 30 nucleotides in length, corresponding to a portion of the target gene sequence. By use of a battery of such allele-specific probes, target nucleic acid amplification products can be screened to identify the presence of a previously identified mutation in the target gene. Hybridization of allele-specific probes with amplified target nucleic acid sequences can be performed, for example, on a nylon filter. Hybridization to a particular probe under stringent hybridization conditions indicates the presence of the same mutation as in the allele-specific probe.

PARP1 probes can also be used to detect mismatches with the wild type gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids (Novack et al., *Proc. Natl. Acad. Sci. USA* 83:586, 1986).

Hybridization probes are generally oligonucleotides which bind through complementary base pairing to all or part of a target nucleic acid. Probes typically bind target sequences lacking complete complementarity with the probe sequence depending on the stringency of the hybridization conditions. The probes can be labeled directly or indirectly, such that by assaying for the presence or absence of the probe, one can detect the presence or absence of the target sequence. Direct labeling methods include radioisotope labeling, such as with $^{32}$P or $^{35}$S. Indirect labeling methods include fluorescent tags, biotin complexes which can be bound to avidin or streptavidin, or peptide or protein tags. Visual detection methods include photoluminescents, Texas red, rhodamine and its derivatives, red leuco dye and 3,3', 5,5'-tetramethylbenzidine (TMB), fluorescein, and its derivatives, dansyl, umbelliferone and the like or with horse radish peroxidase, alkaline phosphatase and the like.

Arrays

In particular embodiments provided herein, arrays can be used to evaluate the presence or absence of SNPs in PARP1. In some examples, the array comprises an oligonucleotide that specifically hybridizes with an PARP1 nucleic acid molecule comprising a SNP of interest. In some embodiments, the array can evaluate the presence of a C at rs1805407 in the PARP1 gene.

Oligonucleotides that specifically hybridize with an PARP1 nucleic acid comprising a SNP do not hybridize to the wild type sequence, such as a T a rs1805407 in the PARP1 gene, or hybridization of the oligonucleotide to the wild type sequence is not detectable. In some embodiments the array comprises two or more oligonucleotides that specifically hybridize with an PARP1 SNP in a non-coding region, such as 1, 2, 3, 4, 5, 6, 7, 8, 9, 10 or more SNPs in a non-coding region of the PARP1 gene. In some examples, the array further includes other oligonucleotides, such as control oligonucleotides or oligonucleotides that specifically hybridize with other SNPs, such as in other genes.

The oligonucleotide probes can further include one or more detectable labels, to permit detection of hybridization signals between the probe and target sequence (such as of a C at rs1805407 in the PARP1 gene.

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides are not amenable to non-specific binding, or when non-specific binding occurs, such materials can be readily removed from the surface without removing the oligonucleotides.

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit low background fluorescence.

The array formats of the present disclosure can be included in a variety of different types of formats. A "format" includes any format to which the solid support can be affixed, such as microtiter plates (e.g. multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide sequences are synthesized separately and then attached to a solid support (see U.S. Pat. No. 6,013,789). In another example, sequences are synthesized directly onto the support to provide the desired array (see U.S. Pat. No. 5,554, 501). Suitable methods for covalently coupling oligonucleotides to a solid support and for directly synthesizing the oligonucleotides onto the support are known to those working in the field; a summary of suitable methods can be found in Matson et al. (*Anal. Biochem.* 217:306-10, 1994). In one example, the oligonucleotides are synthesized onto the support using conventional chemical techniques for preparing oligonucleotides on solid supports (such as see International application publications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

Kits

The oligonucleotide probes and/or primers and compositions including such probes and/or primers of use in the methods disclosed herein can be supplied in the form of a kit. In such a kit, one or more of the oligonucleotide probes and/or primers is provided in one or more containers. An oligonucleotide probe or primer can be provided suspended in an aqueous solution, or as a freeze-dried or lyophilized powder. The container(s) in which the oligonucleotide(s) are supplied can be any conventional container that is capable of holding the supplied form; e.g., microfuge tubes, ampoules, or bottles. In some applications, pairs of primers can be provided in pre-measured single use amounts in individual, typically disposable, tubes or equivalent containers.

In some embodiments, kits can also include the reagents necessary to carry out PCR amplification reactions (including, but not limited to, qPCR reactions). In some examples, the kit can include reagents for DNA sample preparation reagents, appropriate buffers (e.g., polymerase buffer), salts (e.g., magnesium chloride), and deoxyribonucleotides (dNTPs). One or more control sequences for use in the PCR reactions can also be supplied in the kit.

In one embodiment, kits are supplied with instructions. In one specific, non-limiting example, the instructions are written instructions. In another such example, the instructions are provided in electronic format. The instructions may, for example, instruct the user how to use the primers and probes to amplify and detect the nucleic acid sequences using a PCR reaction, and then determine if a sample a particular SNP in non-coding region of a PARP1 gene.

The following examples are provided to illustrate certain particular features and/or embodiments. These examples should not be construed to limit the disclosure to the particular features or embodiments described.

EXAMPLES

The whole genome methylation, gene expression and microRNA assays were done as well as personal genotyping using an entromic-technology designed custom panel of 384 single nucleotide polymorphisms (SNPs) on 65 genes, with 27 functioning in the DNA damage and repair pathways. These data were analyzed using a new method for learning graphical models over mixed-type variables (continuous and discrete) (MGM-Learn; Sedgewick, Benos et al., in preparation). The 250 most variable genes, 264 most variant methylation probes, and 139 SNPs from our panel were selected and used as input on this algorithm.

In the entromic technology based design of the SNP panel, the selection of the rs1805407 for the microarray required that (C/T) base change in this locus results in the maximal difference in the incorporation entropy network, consisting of all genes and all 384 genotyped loci in our custom panel of 65 genes. This process maximized the total difference between the incorporation entropy coherences, computed for reference (consensus) genome (where all 384 loci had major allele) and personal entropy coherences, computed for genomes with experimentally genotyped alleles of all patients. The rationale for this selection method was three-fold: first, it naturally incorporated the assumed interoperability of the genotyped genes in the disease treatment. Second, it was shown that incorporation entropy has direct relationship to the rate with which a DNA molecule is replicated or transcribed, and thus any changes (not necessarily coding variants, but also the SNP's in the non-coding regions) can have impact on the dynamics of the DNA damage recognition and repair network function. Third, as the entromic coherence is determined by the sequence context and details of the DNA motifs in a broad neighborhood of the SNP locus, which determines the thermodynamic properties of all potential interactions with regulatory agents on the studied regions of DNA, this coherence is also capable of identifying the similarities in these important sequence motifs in the complete network of all 384 probe loci, especially with emphasis on their specificity and binding energy with regulatory factors, such as micro-RNA's.

The complete "exome" DNA sequence was generated by concatenation of the ordered coding DNA's from all genes (reference human genome assembly HG 19). For this exome DNA, the matrix of coherences (also called t-homology) between the incorporation entropy vectors was computed, as disclosed in US Published Patent Application No. 2011/0172930 A1 and PCT Publication No. WO 2010033777 A3. From the computed values of incorporation entropy coherences for all positions of exome DNA, the "heat map" representation of the intensity surface of these coherences between all human genes was constructed. These coherences were computed systematically for all possible base-base relationships. For the purpose of visualization, the complete exome DNA was divided into 70 segments of the comparable lengths and the base-resolution values of the incorporation entropy coherences within these segments were averaged. In the resulting heat map, the red color blocks identify exome regions, where gene-gene pairwise encoding relationships exhibit high coherence of the incorporation entropies. Orange, yellow, and cyan represent intermediate incorporation entropy coherence intensities in the declining order.

According to the functional meaning of the entromic physics of DNA, the assayed variants of the DNA-repair pathway genes were selected in the genotyping microarray design as those, for which the transition from major to minor allele generates the maximal impact on the dynamics of the systemic response of the patient's biosystem to the DNA repair pathway function (see and Entromics—thermodynamics of sequence dependent base incorporation into DNA reveals novel long-distance genome organization, Pancoska, P. et al., arXiv:1206.2070 [q-bio.OT], 2012). Entromics characterizes this impact on the pathway dynamics by the sum of complete network of incorporation entropy (energy) differences between the incorporation entropies, computed both for position-position (within the gene) and inter-gene position-position full genome coherences for the personal genomic profiles of each individual patient relatively to the common reference (all-major-allele) genome. These differences are by definition maxima in the regions of the coherence matrix with the maximal values of the incorporation entropy coherences. The SNPs selected for the microarray assay in this application are unique by forming the maximal spanning network in the coherence matrix of all testable variants, known for the genes in the selected pathways. The functional uniqueness of this method of assay design guaranties that the variants in the assayed positions will have the maximal differential impact on the dynamics of probed pathways.

The functional response of the DNA repair pathway to the assayed genomic variants should be also reflected in the characteristic patterns of the gene expressions and regulation-related patterns, such as methylation levels. Using the same arguments as above, these additional unique patterns should be found for the genes (not necessarily DNA-repair involved), which are in strong incorporation entropy coherences with one or more genes from the DNA repair pathway.

In general, identifying biomarkers that best characterize patient subpopulations in response to various drugs is considered to be the next frontier for cancer precision medicine. Current methods for biomarker identification operate on a single dataset or data type (either continuous or discrete variables only) and cannot seamlessly combine different datasets. A new integrative strategy was developed to identify biomarkers that refine patient stratification based on collected omics data (including gene expression, methylation and SNP data) and clinical information. This strategy is based on a new graphical model learning algorithm, MGM-Learn (Mixed Graphical Model Learning), which can infer direct (causal) associations over a compendium of mixed data types (i.e., continuous and discrete variables), like the ones obtained from genomic, genetic and clinical data. The resulting network structure represents conditional dependencies between variables, thus allowing one to investigate disease pathways and mechanisms, and perform classification tasks such as patient stratification, biomarker selection, and disease prognostication or prediction.

As disclosed below, MGM-Learn was applied to metastatic melanoma, which remains an excellent model for chemotherapy resistance given its refractory nature, despite the fact that current management of metastatic melanoma can also be achieved with non-chemotherapy based strategies (e.g., targeted and immune-based therapies). Among various features that were directly linked to response to treatment, a SNP was identified in the PARP1 gene. This SNP was highly predictive of resistance to chemotherapy. The impact of this PARP1 variant on PAPR inhibitor (PARPi) sensitivity was characterized, and its utility as a predictive biomarker of PARPi sensitivity was demonstrated. Given the role of PARP1 in DNA repair, this SNP is a biomarker for PARPi sensitivity, and can be used to guide patient selection for treatment protocols incorporating PARPi's singly or in combination with chemotherapeutic agents, such as alkylating agents.

Example 1

Novel Algorithm for Learning Mixed Graphical Models (MGM-Learn)

The term Mixed Graphical Models (MGM) refers to graphical models that are learned over variables of mixed type, i.e., continuous and discrete variables (binary, categorical, ordinal). This is an understudied problem, which only recently has attracted attention and only for undirected graphs (Lee J & Hastie T (2013) *Journal of Machine Learning Research* 31:388-396; Chen S, Witten D, & Shojaie A (2014) *arXiv preprint arXiv*:1311.0085v2 [*stat.ME*]; Cheng J, Levina E, & Zhu J (2013) *arXiv preprint arXiv:* 1304.2810v1 [*stat.ML*]; Fellinghauer B, Buehlmann P, Ryffel M, von Rhein M, & Reinhardt J D (2013) *Computational Statistics and Data Analysis* 64:132-152; Tur I & Castelo R (2012) in *Probabilistic Graphical Models* (*PGM*) 2012 (Granada, Spain); Yang E, Baker Y, Ravikumar P, Allen G, & Liu Z (2014) *J Mach Learn Res* 33:1042-1050; Romero V, Rumi R, & Salmeron A (2006) *International Journal of Approximate Reasoning* 42(1-2):54-68; Bøttcher SG (2001) in *Eighth International Workshop on Artificial Intelligence and Statistics* (Key West, Fla.), pp 149-156). A workflow, named MGM-Learn, was developed for learning a probabilistic network of partially causal graph (directed and undirected edges) over mixed type variables in a quick and efficient way. MGM-Learn is modular and consists of three steps (FIG. 1). First, data are pre-filtered (if needed) and normalized; then the undirected graph is learned using a fast method (5); and finally edges are oriented using exhaustive local searches over small subsets of variables (in the case, PC-Stable (Colombo D & Maathuis M H (2014) *Journal of Machine Learning Research* 15:3741-3782) was utilized for the local searches). Since the acyclicity assumption was not imposed, the final graph is partially directed (partially causal). Detailed description of the algorithm is presented below. The modularity of the pipeline was emphasized, so alternative methods can be easily implemented and used in each step.

Example 2

Single Nucleotide Polymorphism (SNP) Panel Selection

In order to be cost-effective, a custom-made melanoma/ cancer ILLUMINA® SNP panel was created. First, literature searches were performed and expert knowledge of the current cancer and melanoma biology was used to select relevant pathways and their corresponding genes. In this step, the following pathways were considered: DNA repair, MAPK, AKT, PI3K and mTOR signaling, immune response, DNA methylation, cell cycle, apoptosis, and signal transduction via erB signaling. Sixty-five genes were identified in these pathways and all SNPs were retrieved from dbSNP in the ±10 Kbp region around each of them. SNP filtering followed, which included the following criteria: (1) minor allele frequency (MAF) <10%; (2) screening using the ILLUMINA® Assay Design Tool (ILLUMINA®, San Diego, Calif.) to ensure SNPs can be incorporated in an optimal custom array design. The remaining SNPs of each gene were in strong LD (in general, $r^2 \geq 0.8$). Approximately six SNPs per gene (where possible) were selected to complete the 384 SNP ILLUMINA® design. After data collection, quality control and initial analysis further reduced this dataset to 139 SNPs for the following reasons: no variation observed across samples, poor SNP call rate (less than 90%) or failed Hardy-Weinberg Equilibrium.

Example 3

Figure 2B:
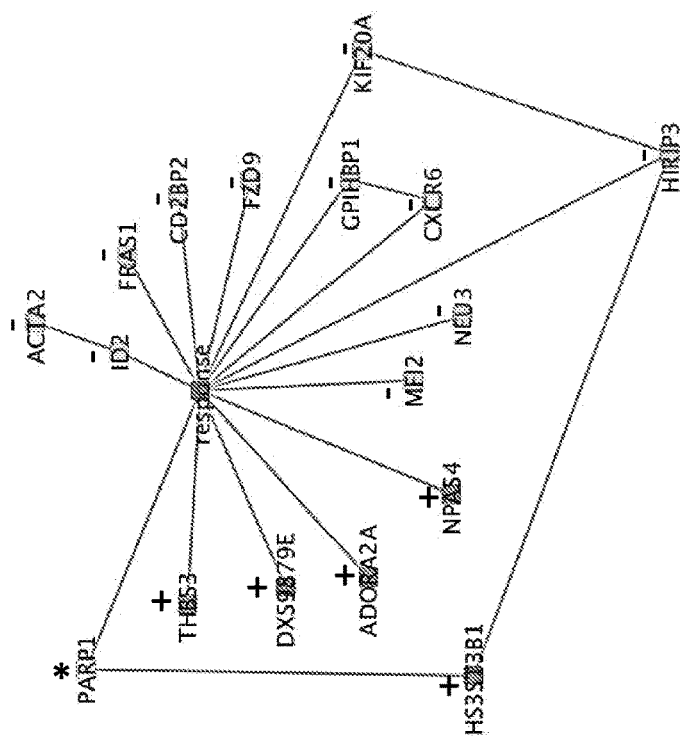
FIGS. 2A-2B. Conditional Gaussian sub-network around response to treatment with edge filter (FIG. 2A). The plus (+) represents methylation probes, the minus (−) represents mRNA expression probes and the asterisk (*) represents SNPs. Heatmap of variables directly connected to response to and temozolomide (TMZ) treatment (FIG. 2B).
Figure 2A:
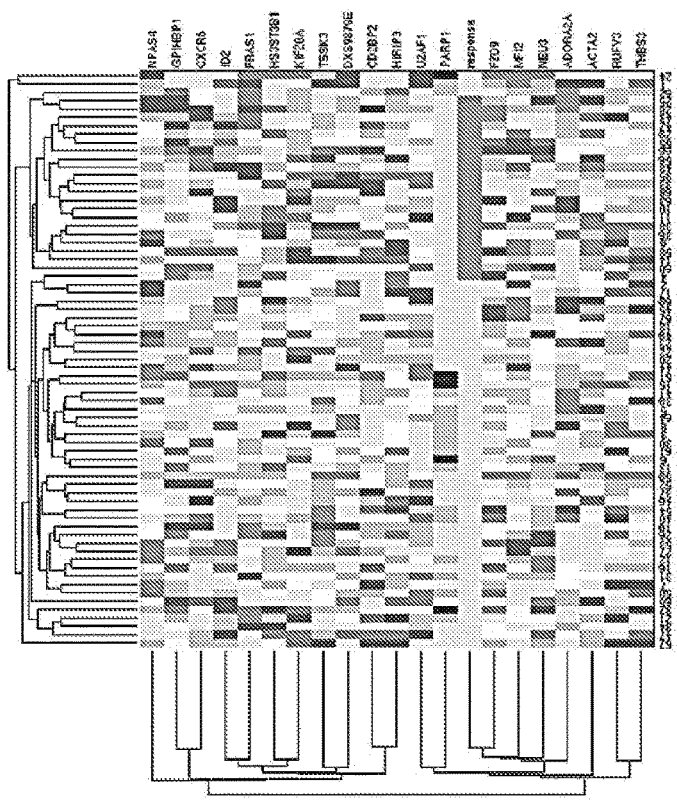

Identifying Predictive Markers of Treatment for Metastatic Melanoma Patients Using MGM-Learn The melanoma dataset consisted of whole genome gene expression, microRNA expression, DNA methylation, and data from the selected SNP panel. MGM-Learn was used to learn a network over the top 1000 features most correlated (pairwise) with "response" to treatment clinical variable, a binary variable indicating response/no response to temozolomide (TMZ) treatment dichotomized at presence of a response or stability of disease at 4 months of therapy. The 1,000 most correlated features in the input dataset included 557 mRNA expression probes, 425 methylation probes, 14 miRNA probes and 4 SNPs. BRAF mutation status was also included in the input variables to see if it had an effect on any of the features linked to response, although its direct correlation with it in this dataset was poor ($R^2=0.025$). The largest interconnected output network included 20 features connected to the response variable in our initial (undirected) learned network (FIG. 2A). It was emphasized that these features were connected to the response variable not only because they have high pairwise correlation with it (FIG. 2B), but also because they are dependent on response even when conditioned on all other variables included in the input. In this sense, they represent direct (causal) interactions and not simple biomarkers. From the 20 features initially connected to response, 15 were left connected after causal filtering (FIG. 2A, black lines). A methylation feature for DXS9879E (LAGE3) is one of them, and it has been linked to survival in non-small cell lung cancer (Lokk K, et al. (2012) *PloS one* 7(6):e39813.). Notably, this important feature is not present in the top 20 (pairwise) correlated features with response. Also, ID2 expression is also directly linked to response, and is known to induce growth and proliferation in squamous cell carcinoma Wang C, et al. (2012) *Chinese journal of cancer* 31(9):430-439). Contrary to previous reports in hematologic malignancies (16), the data show that both hypermethylation of LAGE3 and overexpression of ID2 are indicative of improved response to TMZ.

Example 4

Figure 5:
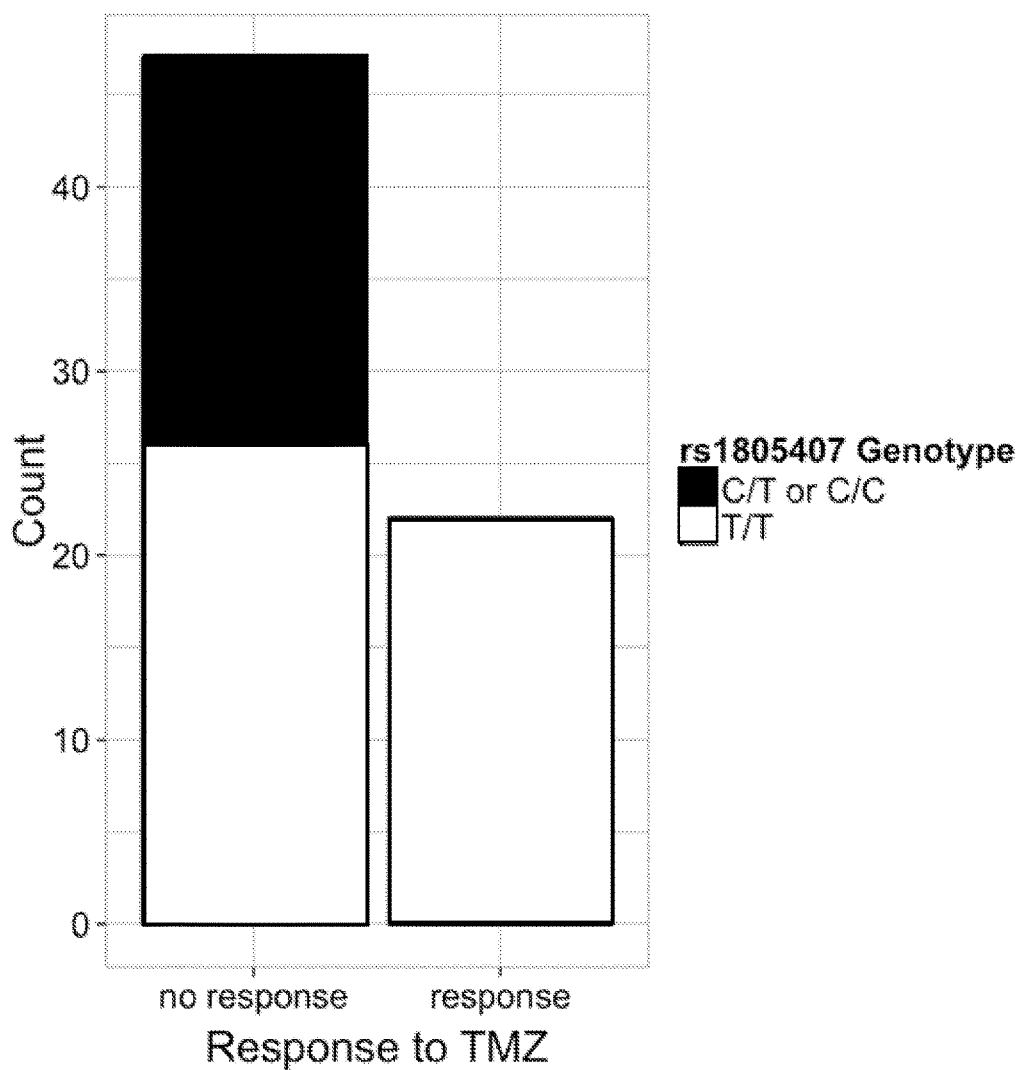
FIG. 5. Association of SNP rs1805407 to response to TMZ treatment

SNP Rs1805407 in PARP1 is Strongly Associated with Worse Outcome in Melanoma Patients SNP rs1805407 (PARP1) is the only SNP in the dataset that was directly linked to response. It was found that this SNP was an excellent predictor of worse outcome since all 21 patients that had the SNP (C/T or C/C) showed no response to TMZ treatment (FIG. 5) (pvalue=4.6e-5). Because of the strong direct (causal) association, the role that PARP1 plays in repairing TMZ mediated DNA damage, and the availability of PARP inhibitors, it was decided to investigate this finding further. rs1805407 is located on the $2^{nd}$ intron of PARP1-4 Kbp downstream of the PARP1 transcription start site and 35 bp downstream of the 3' splice site of exon 2. SNAP (Johnson A D, et al. (2008) *Bioinformatics* 24(24):2938-2939) was used to find other SNPs in strong linkage disequilibrium (LD) with rs1805407. The CEU population panel of 1000 Genomes pilot 1 contained 51 variants in perfect LD ($r^2=1$) (Table 1) with the selected variant. Of these, two are upstream of the transcription start site (TSS).

TABLE S1

| PARP1 SNPs in LD with rs1805407. | | | | | |
|---|---|---|---|---|---|
| SNP | Distance | $R^2$ | D' | Chr | Coord_hg18 GeneVariant |
| rs3219031 | 437 | 1 | 1 | chr1 | 224656019 INTRONIC |
| rs3219027 | 580 | 1 | 1 | chr1 | 224657036 INTRONIC |
| rs6701634 | 1792 | 1 | 1 | chr1 | 224654664 INTRONIC |
| rs3754370 | 2445 | 1 | 1 | chr1 | 224658901 INTRONIC |
| rs3768347 | 2912 | 1 | 1 | chr1 | 224659368 INTRONIC |
| rs3768346 | 3021 | 1 | 1 | chr1 | 224659477 INTRONIC |
| rs7522351 | 3435 | 1 | 1 | chr1 | 224659891 INTRONIC |
| rs7525191 | 3438 | 1 | 1 | chr1 | 224659894 INTRONIC |
| rs4653732 | 4273 | 1 | 1 | chr1 | 224660729 INTRONIC |
| rs10799349 | 4317 | 1 | 1 | chr1 | 224652139 INTRONIC |
| rs7542788 | 4530 | 1 | 1 | chr1 | 224651926 INTRONIC |
| rs7548007 | 4553 | 1 | 1 | chr1 | 224651903 INTRONIC |
| rs4653733 | 4780 | 1 | 1 | chr1 | 224661236 INTRONIC |
| rs60698376 | 5024 | 1 | 1 | chr1 | 224661480 N/A |
| rs4653731 | 5861 | 1 | 1 | chr1 | 224650595 INTRONIC |
| rs2077197 | 6206 | 1 | 1 | chr1 | 224662662 UPSTREAM |
| rs12240196 | 6350 | 1 | 1 | chr1 | 224650106 INTRONIC |
| rs59672299 | 7760 | 1 | 1 | chr1 | 224664216 N/A |
| rs1073991 | 8759 | 1 | 1 | chr1 | 224647697 INTRONIC |
| rs2136876 | 8880 | 1 | 1 | chr1 | 224647576 INTRONIC |
| rs1000033 | 9446 | 1 | 1 | chr1 | 224647010 INTRONIC |
| rs6665208 | 9541 | 1 | 1 | chr1 | 224665997 UPSTREAM |
| rs1002153 | 9646 | 1 | 1 | chr1 | 224646810 INTRONIC |
| rs2280712 | 9740 | 1 | 1 | chr1 | 224646716 INTRONIC |
| rs1805405 | 9812 | 1 | 1 | chr1 | 224646644 SPLICE_SITE, INTRONIC |
| rs6679573 | 11114 | 1 | 1 | chr1 | 224667570 INTERGENIC |
| rs10915987 | 11848 | 1 | 1 | chr1 | 224668304 INTERGENIC |
| rs3219043 | 12239 | 1 | 1 | chr1 | 224644217 INTRONIC |
| rs77173384 | 12382 | 1 | 1 | chr1 | 224668838 N/A |
| rs28407557 | 12564 | 1 | 1 | chr1 | 224669020 INTERGENIC |
| rs4653445 | 12927 | 1 | 1 | chr1 | 224643529 INTRONIC |
| rs2293464 | 13537 | 1 | 1 | chr1 | 224642919 INTRONIC |
| rs12068460 | 13912 | 1 | 1 | chr1 | 224670368 INTERGENIC |
| rs3219053 | 15279 | 1 | 1 | chr1 | 224641177 INTRONIC |
| rs1805408 | 16431 | 1 | 1 | chr1 | 224640025 INTRONIC |
| rs3219058 | 17039 | 1 | 1 | chr1 | 224639417 INTRONIC |
| rs6681537 | 19603 | 1 | 1 | chr1 | 224676059 INTERGENIC |
| rs3219073 | 20458 | 1 | 1 | chr1 | 224635998 INTRONIC |
| rs2271343 | 22270 | 1 | 1 | chr1 | 224634186 INTRONIC |
| rs732284 | 22825 | 1 | 1 | chr1 | 224633631 INTRONIC |
| rs3219115 | 32892 | 1 | 1 | chr1 | 224623564 INTRONIC |
| rs752308 | 38327 | 1 | 1 | chr1 | 224618129 INTRONIC |
| rs747658 | 38655 | 1 | 1 | chr1 | 224617801 INTRONIC |
| rs747659 | 39092 | 1 | 1 | chr1 | 224617364 INTRONIC |
| rs6664761 | 39642 | 1 | 1 | chr1 | 224616814 INTRONIC |
| rs2282400 | 42834 | 1 | 1 | chr1 | 224613622 DOWNSTREAM |
| rs6675427 | 45851 | 1 | 1 | chr1 | 224610605 DOWNSTREAM |
| rs6675327 | 45924 | 1 | 1 | chr1 | 224610532 DOWNSTREAM |
| rs6661762 | 46142 | 1 | 1 | chr1 | 224610314 DOWNSTREAM |
| rs1991865 | 48782 | 1 | 1 | chr1 | 224607674 INTERGENIC |
| rs12092726 | 50806 | 1 | 1 | chr1 | 224605650 INTERGENIC |
| rs3219023 | 1223 | 0.947 | 1 | chr1 | 224657679 INTRONIC |
| rs7531668 | 6186 | 0.945 | 1 | chr1 | 224662642 UPSTREAM |
| rs12025487 | 15060 | 0.945 | 1 | chr1 | 224671516 INTERGENIC |
| rs1109032 | 28430 | 0.945 | 1 | chr1 | 224628026 INTRONIC |
| rs3754375 | 28768 | 0.945 | 1 | chr1 | 224627688 INTRONIC |
| rs4653735 | 10521 | 0.891 | 1 | chr1 | 224666977 UPSTREAM |
| rs878367 | 52311 | 0.891 | 1 | chr1 | 224604145 INTERGENIC |
| rs7527192 | 6246 | 0.838 | 1 | chr1 | 224662702 UPSTREAM |

Specifically, rs6665208 is 3573 bases upstream of the PARP1 TSS and overlaps with ENCODE ChIP peaks for MAFF and MAFK. rs2077197 is 238 bases upstream and overlaps peaks for CTCF, HA-E2F1, AP-2alpha, ZBTB7A, Pol2, CEBPB and YY1. Another SNP (rs1805405) is also in perfect LD with rs1805407 ($R^2=1$) and is annotated as a 'Splice region variant' because it is located 5 base pairs (bp) upstream from the splice site between intron 2 and exon 3. Finally, a strong dependence was found between rs1805407 and two other SNPs that have been previously associated with melanoma susceptibility: rs3219090 ($D'=1$, $R^2=0.43$) and rs2249844 ($D'=1$, $R^2=0.46$). Due to high LD values with rs1805407 none of these SNPs were included in our original SNP dataset.

Example 5

SNP Rs1805407 is Related to Decreased Cytotoxicity of Alkylating Agents in Cell Lines with the Variant The previous results showed that rs1805407 is associated with worse outcome of melanoma patients treated with TMZ. Given that TMZ damages the DNA and PARP1 has a critical role in DNA repair, one plausible hypothesis is that rs1805407 is either associated with increased PARP1 activity or decreased PARP1 trapping after treatment with alkylating agents (Murai J, et al. (2012) Cancer Res 72(21): 5588-5599). The role of rs1805407 in cell response to various drugs was investigated. The NCI-60 CELLMINER™ database (Reinhold W C, et al. (2012) Cancer Res 72(14):3499-3511) contains the response of 60 cell lines to ~50,000 compounds. It was evaluated whether drugs affect differentially the cell lines that have at least one copy of rs1805407 (C/T or C/C) vs wild type (T/T). The Affymetrix 500 k SNP arrays used by CELLMINER™ did not include rs1805407, so we used the k-nearest neighbors method with three of the 51 perfectly correlated variants with probes in the array (rs1073991, rs10799349 and rs3219027) to infer the rs1805407 genotype in each cell line. Analysis of the $IC_{50}$ values in cell lines predicted to have at least one allele of rs1805407 (n=23; C/T or C/C) vs wild type (n=37; T/T) showed statistically significant resistance or sensitivity to four compounds, three of which are alkylating agents with action similar to TMZ (notably, TMZ is not included in the NCI-60 dataset) (Table 2).

TABLE 2

Drug compounds with differential $IC_{50}$ values on wt vs SNP cell lines for rs1805407. $IC_{50}$ values derived from NCI60. Statistical significance was assessed with Wilcoxon rank sum test.

| NSC | Name | FDA status | u | p |
|---|---|---|---|---|
| 26271 | Cyclophosphamide | FDA approved | 175 | 0.01432674 |
| 157035 | Parthenolide | FDA approved | 148 | 0.020851472 |
| 683863 | Hydroxymethylacylfulvene, Irofulven | FDA approved | 267.5 | 0.021374401 |
| 409962 | Carmustine | FDA approved | 294 | 0.032279804 |

Increased resistance was observed for Carmustine and Cyclophosphamide (Mann-Whitney p-value=0.01 and 0.02, respectively) both classical DNA damaging alkylating agents (the repair of which is PARP1 dependent); and Parthenolide, a compound that induces apoptosis in acute myelogenous leukemia (AML) and progenitor cells (Guzman M L, et al. (2005) Blood 105(11):4163-4169). Increased sensitivity was observed for Irofluven (p=0.02), an alkylating agent that inhibits DNA replication (Wang Y, Wiltshire T, Senft J, Reed E, & Wang W (2007) Biochemical pharmacology 73(4):469-480). In addition cell lines containing the PARP1 SNP showed a slight increase in sensitivity to the PARPi olaparib used as a single agent. These results are compatible with the hypothesis that SNP rs1805407 (or one of the 51 SNPs in perfect LD with it) can cause increased PARP1 activity or decreased PARP1 trapping, thus helping to repair the damage caused by TMZ and potentially eliminating the additional cytotoxic effects of PARP-DNA complexes induced by PARP trapping. PARP trapping could explain both observations of differential chemotherapy response and PARPi effects.

Example 6

SNP Rs1805407 is Related to PARP Inhibitor Potentiation of Alkylating Agent Cytotoxicity Experimental validation of the association of a SNP to increased PARP1 activity in patient-derived tissues is not straightforward because PARP1 is an inducible enzyme and its activity may depend on the timing of the biopsy with respect to prior therapies. Alternatively, one can use cell lines to test whether PARP1 activity (or PARP1 trapping) affects the response to alkylating agents in a SNP-dependent way. This can be done by blocking PARP1 in cells with or without the SNP after treatment. If rs1805407 increases PARP1 activity or makes cells more susceptible to PARP1 trapping then cell lines with the SNP will be more sensitive to complete PARP1 inhibition.

Fifteen cell lines (Table 3) were identified from various tumor types, which had reported activity of alkylating agents (such as TMZ) alone or in combination with one of PARPi's (CEP-6800, AG14361, NU1085, NU1025 or ABT-888) (Calabrese C R, et al. (2004) JNCI Journal of the National Cancer Institute 96:56-67; Davidson D, Wang Y, Aloyz R, & Panasci L (2013) Investigational new drugs 31:1-14; Delaney C, Wang L, & Kyle S (2000) Potentiation of Temozolomide and Topotecan Growth Inhibition and Cytotoxicity by Novel Poly(adenosine Diphosphoribose) Polymerase Inhibitors in a Panel of Human Tumor Cell Lines. Clinical cancer; Miknyoczki S & Jones-Bolin S (2003) Chemopotentiation of Temozolomide, Irinotecan, and Cisplatin Activity by CEP-6800, a Poly(ADP-Ribose) Polymerase Inhibitor. Molecular cancer 371-382; Tentori L, et al. (2003) Molecular pharmacology 63:192-202; Wang L, et al. (2012) Investigational new drugs 30:2113-2120).

TABLE 3

PARP1 SNP rs1805407 genotyping analysis of a panel of human cancer cell lines. Most (6 out of 7) of the cell lines reported in the literature to be "resistant" to chemotherapy + PARPi combination treatment were WT for the rs1805407 locus. Similarly, almost all (7 out of 9) of the cell lines reported to be "sensitive" had at least one copy of T in this locus. Cell line was considered "sensitive" when chemopotentiation ratio was ≥ 2.

| Cell line | Potentiation of response to chemotherapy + PARP inhibition (from literature) | Tumor type | Genotype for PARP1 SNP | REFS |
|---|---|---|---|---|
| LoVo | R | Colon | T/T | (30, 55) |
| SW620 | R | Colorectal | T/T | (30, 55) |

TABLE 3-continued

PARP1 SNP rs1805407 genotyping analysis of a panel of human cancer cell lines. Most (6 out of 7) of the cell lines reported in the literature to be "resistant" to chemotherapy + PARPi combination treatment were WT for the rs1805407 locus. Similarly, almost all (7 out of 9) of the cell lines reported to be "sensitive" had at least one copy of T in this locus. Cell line was considered "sensitive" when chemopotentiation ratio was ≥ 2.

| Cell line | Potentiation of response to chemotherapy + PARP inhibition (from literature) | Tumor type | Genotype for PARP1 SNP | REFS |
|---|---|---|---|---|
| H522 | R | Lung | T/T | (30) |
| HT-29 | R | Colon | T/T | (30) |
| SKOV-3 | R | Ovarian | T/T | (30) |
| LS174T | S | Colon | T/T | (30) |
| HCT-116 | S | Colon | T/T | (56) |
| MDA-MB-231 | R | Breast | C/T | (30) |
| MCF-7 | S | Breast | C/T | (30) |
| Calu-6 | S | Lung | C/T | (57) |
| M14 | S | Melanoma | C/T | NCI60 and (58) |
| A549 | S | Lung | C/T | (30) |
| H460 | S | Lung | C/T | (59) |
| SK-Mel-2 | S | Melanoma | C/C | NCI60 |
| A2780 | S | Ovarian | C/T | (30) |

S: sensitive; R: resistant.

Quantitative polymerase chain reaction (qPCR) was used to confirm the rs1805407 genotypes in these cell lines. The cell lines were classified as "resistant" to the combination of TMZ with PARPi if the reported experiments did not show potentiation of cytotoxicity of TMZ when a PARPi was added; likewise, cell lines that showed significant potentiation of TMZ cytotoxicity with PARPi were classified as sensitive. Interestingly, seven of eight cell lines that had at least one C in position rs18050407 were sensitive (the exception being breast MDA-MB-231, which actually was found to be sensitive in our experiments, see below), and five of seven cell lines that were WT (T/T) were resistant (exceptions are colon LS174T and HCT-116). Overall, these significant results (p=0.02, Chi-square) are consistent with the melanoma cohort data. Without being bound by theory, this suggested that PARP1 SNP rs1805407 (C/T) confers resistance to chemotherapy through increased PARP1 activity or decreased PARP1 trapping. This same functional effect manifests as increased sensitivity to PARPi's alone but more impressively in combination.

To further test this theory similar experiments were performed on nine cell lines from various histologies (melanoma, lung, colon, ovarian, and breast cancer): four were wild type (T/T) and five were C/T for SNP rs1805407 (Table 4).

TABLE 4

Results from MMS treatment of cell lines with and without PARP1 inhibitor (ABT-888). The data from the MTT assays were expressed as mean ± standard deviation (SD). The ratio between the IC50 means of MMS treatment alone and in combination with ABT-888 was calculated for each cell line. A Potentiation factor (ratio) ≤1 indicates no chemo-potentiation.

| Cell line | Tissue origin | PARP1/SNP genotype | MMS IC50 (μM) | MMS + ABT-888 IC50 (μM) | Potentiation factor | p-value: |
|---|---|---|---|---|---|---|
| FEMX | melanoma | T/T | 166.3 (±20.2) | 176.0 (±40.4) | 0.945 | 0.626 |
| A375 | melanoma | T/T | 306.0 (±22.1) | 283.3 (±33.5) | 1.080 | 0.172 |
| H-522 | lung | T/T | 577.7 (±56.8) | 745.3 (±68.6) | 0.775 | 0.147 |
| SW620 | colon | T/T | 299.4 (±37.0) | 449.4 (±89.1) | 0.666 | 0.047 |
| M14 | melanoma | C/T | 520.8 (±63.4) | 359.8 (±56.7) | 1.447 | 0.005 |
| A549 | lung | C/T | 254.8 (±23.9) | 143.9 (±37.8) | 1.771 | 0.002 |
| A2780 | ovarian | C/T | 190.0 (±41.0) | 80.8 (±14.7) | 2.351 | 0.003 |
| MCF-7 | breast | C/T | 193.3 (±24.7) | 124.5 (±46.2) | 1.553 | 0.017 |
| MDA-MB-231 | breast | C/T | 259.8 (±22.9) | 171.9 (±33.2) | 1.511 | 0.001 |

Figure 3:
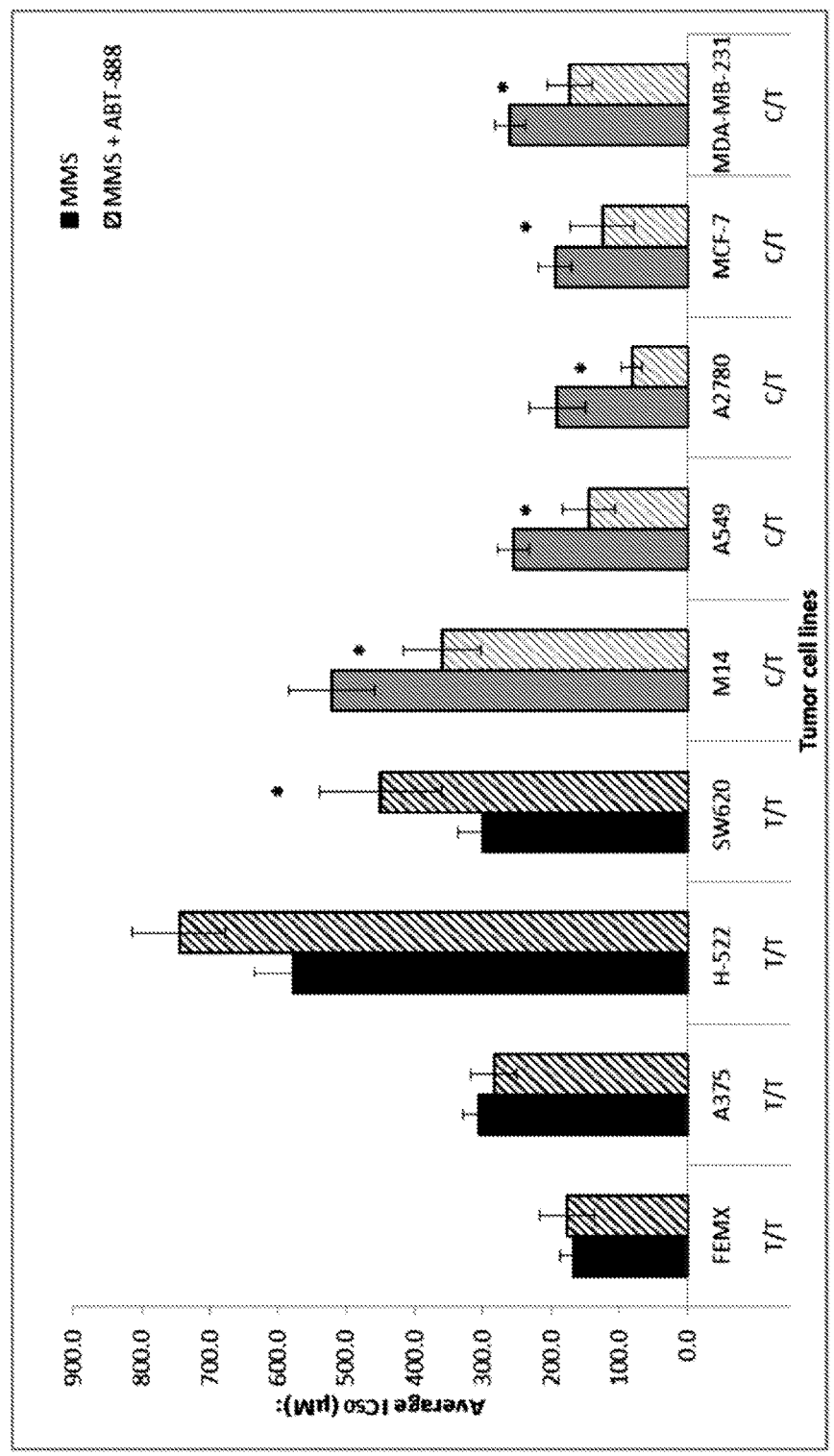
FIG. 3. PARP1/SNP genotype is predictive of PARP1i+MMS combination treatment efficacy. Plot of the $IC_{50}$ values. methyl methanesulfonate (MMS): alkylating agent used; ABT-888: PARP1 inhibitor used; left bars: MMS only; right bars: MMS+ABT-888. Dark grey bars: wild type (T/T) for rs1805407; light grey bars: heterozygotes (C/T). Star indicates that combination treatment (MMS+ABT-888) has significantly different effect than alkylating agent alone ($p<0.05$, Student's t-test, paired two-tailed).

It was noted that MDA-MB-231 was reported as resistant in the literature (30) but was sensitive, which is consistent with other results in the presence of the variant (C/T). Alkylating agent MMS was used to mimic TMZ therapy; and ABT-888 was used to inhibit PARP activity. PARPi potentiates the cytotoxic effect of the chemotherapeutic agent (MMS) in mutated PARP1/SNP cell lines but not in WT PARP1/SNP cell lines. All five C/T cell lines were found to be significantly more sensitive to the combination treatment; while for three of the four wild type (T/T) cell lines the combination treatment had no effect (FIG. 3). Notably, the wild type (T/T) even seemed to confer resistance to PARP inhibition that appeared to decrease the efficacy of MMS, and in one case (SW620) it significantly increased the $IC_{50}$ of MMS suggesting potential antagonism.

Example 7

PARP Inhibitors and Alkylating Agents Exhibit Synergy in Relation to SNP Rs1805407 and Antagonism in Relation to the Wild-type Genotype Next, the potential combinatorial effects of alkylating agent (MMS) and PARPi (ABT-888) was investigated on cell lines with different rs1805407 genotypes. Exponentially dividing cells were exposed for 72 h to increasing concentrations of ABT-888 (0-500 μM) or MMS (0-1 mM) alone (single drug treatment) or with ABT-888/MMS (drug combination treatment) combined at a fixed ratio based on their corresponding $IC_{50}$s. Cell survival was assessed by 3-(4,5-dimethylthiazol-2-yl)-2,5-diphenyltetrazolium bromide, yellow tetrazole (MTT) assay as previously described. The Chou-Talalay combination index (C.I.) (Chou T C & Talalay P (1984) *Advances in enzyme regulation* 22:27-55) of ABT-888 with MMS was determined in four established cell lines: two with the variant C/T (A2780-ovarian cancer and M14-melanoma) and two wild-type T/T (SW620-colon cancer and H522-lung cancer). The C.I. provides insight into whether the effect of both agents is additive (C.I.=1), synergistic (C.I.<1), or antagonistic (C.I.>1). Statistically significant synergy was observed between ABT-888 and MMS in the two cell lines with the C/T variant (strong and moderate effect in A2780 and M14, respectively; Table 1). In WT cell lines the effect is additive at best (H522). Interestingly, the SW620 cell line had decreased cytotoxicity of MMS after the addition of ABT-888. This might indicate antagonism as the C.I. was statistically significantly higher than 1. The graphs of the cytotoxic effects of MMS alone or in combination with ABT-888 PARP inhibitor are presented in FIG. 6.

Example 8

SNP Rs1805407 is Linked to Higher Expression of PARP1-003 Splicing Variant

Thus it was established that PARP1 SNP rs1805407 is directly linked to worse response to alkylating therapy in metastatic melanoma patients and cell lines. Furthermore, it was shown that there is a synergistic effect of alkylating agents and PARPi's in cell lines with the SNP.

Figure 4:
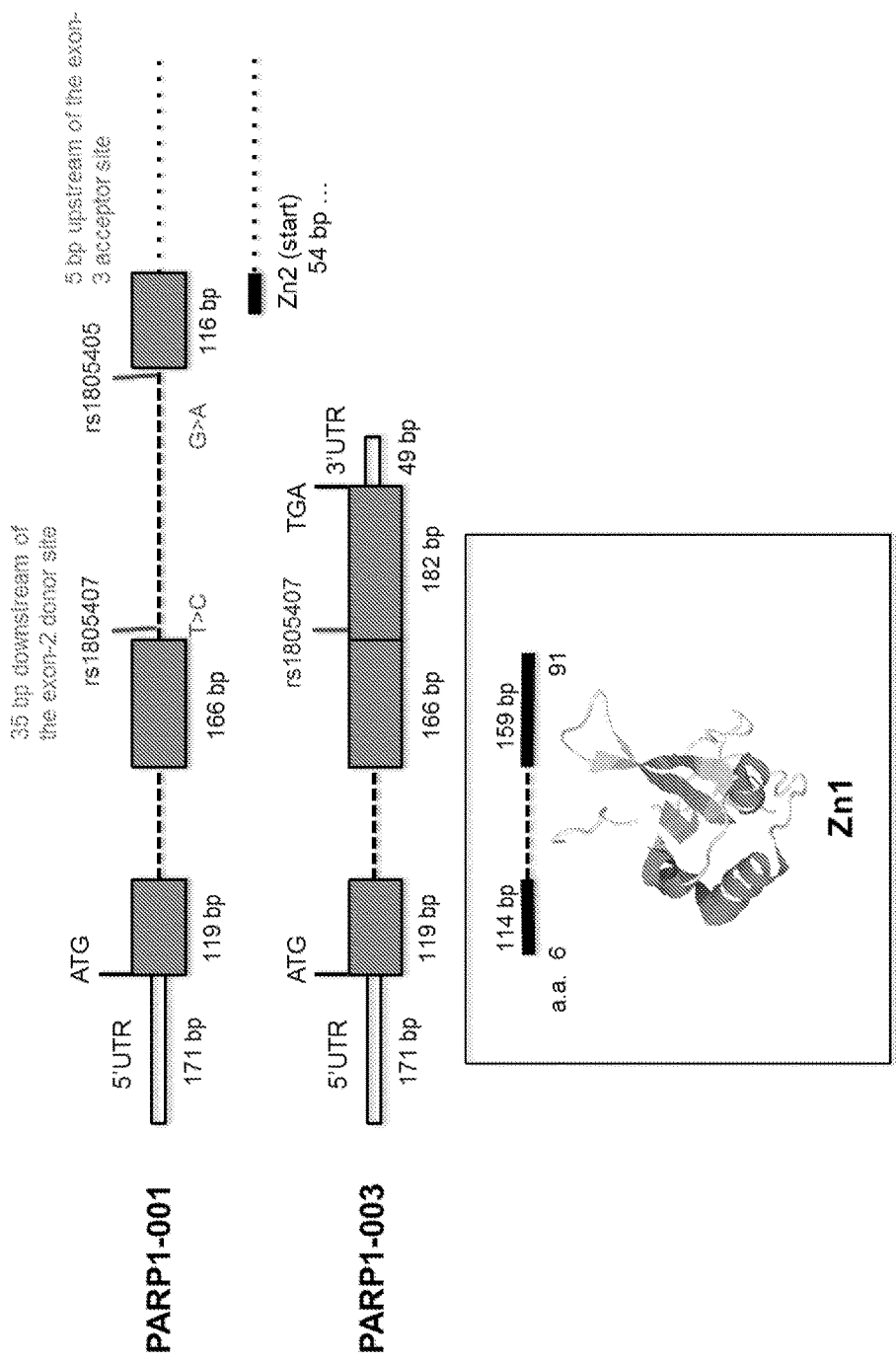
FIG. 4. Genomic structure of the first exons of PARP1 main transcript (PARP1-001) and its truncated alternative spliced one (PARP1-003) found to be increased in patients with at least one minor allele in SNP rs1805407. Note that rs1805407 and rs1805405 are in perfect LD ($r^2$-1). PARP1-003 has only Zn1 (structure from PDB:2L30).

Analysis of the melanoma cohort and the TCGA melanoma data showed that PARP1 expression does not increase significantly in metastatic versus non-metastatic patients. According to Ensembl however, there are ten PARP-1 alternatively spliced transcript isoforms, four of which are protein coding: the predominant form, PARP1-001, and PARP1-003, PARP1-005 and PARP1-201. In the predominant form of PARP1 transcript rs1805407 is located 35 bases downstream of the end of exon 2. PARP1-003 (ENST00000366790) is interesting because it misses the splice site at the end of exon 2 (chr1:226,590,083; hg19) and continues translating another 59 amino acids before it reaches a stop codon (FIG. 4). Thus the resulting protein, PARP1-003, is short (155 amino acids instead of 1,014) and contains only the first of the two zinc finger domains and none of the two catalytic PARP1 domains (Eustermann S, et al. (2011) *J Mol Biol* 407(1):149-170). In PARP1-003 isoform, rs1805407 corresponds to a substitution of an arginine for a lysine at amino acid position 123.

To further study the potential role of rs1805407 in the function of PARP1, the abundances of the various PARP1 isoforms in 418 TCGA ovarian cancer patients (Level 2 data) were calculated and compared between groups of patients with and without rs1805407. This analysis found a strong association between rs1805407 and the abundance of the PARP1-003 isoform. Carriers of at least one variant allele (N=131) have small but statistically significantly higher ratio of PARP1-003 abundance to PARP1-001 abundance compared to non-carriers (N=287) (p=3e-05, Mann Whitney U test). This ratio ranges from 0.12% for non-carriers to 0.25% for SNP homozygotes. Similar, but less significant, results were observed in the 293 TCGA metastatic melanoma patients.

Application of different therapies in well-defined subgroups of patients is precision medicine for cancer as well as other diseases. A method is disclosed herein for analyzing multi-modal biomedical and clinical data, which discovered a novel biomarker (SNP rs1805407 in PARP1 gene) that can be used to identify patients who respond poorly to chemotherapy and potentially more favorably to PARP inhibition.

PARP-1 acts as a "molecular sensor" to identify DNA single strand breaks. It is then recruited and activated as a homodimer in a fast reaction which is amplified 10 to 500-fold with formation of poly-(ADP-ribose) (PAR) polymers within 15 to 30 seconds. Upon binding to a damaged strand via its zinc finger DNA-binding domain, PARP-1 undergoes a conformational change inducing the C-terminal catalytic domain to transfer ADP-ribose moieties from cellular nicotinamide-adenine-dinucleotide (NAD+) to protein acceptors, including the central auto-modification domain of PARP1 itself. AutoPARylation of PARP1 and PARP2, and PARylation of chromatin proteins promote the recruitment of DNA repair factors (Schreiber V, Dantzer F, Ame J C, & de Murcia G (2006. *Nat Rev Mol Cell Biol* 7(7):517-528: Masson M, et al. (1998) *Mol Cell Biol* 18(6):3563-3571; El-Khamisy S F, Masutani M, Suzuki H, & Caldecott K W (2003) *Nucleic Acids Res* 31(19):5526-5533). Because of the high negative charge of PAR polymers, extensive autoPARylation of PARP1 and PARP2 leads to their dissociation from DNA, which is required for DNA repair completion (Satoh M S & Lindahl T (1992) *Nature* 356 (6367):356-358). The impact of PARP inhibition on cancer cells seems to be more profound than could be explained by catalytic inhibition of PARP.

This SNP was identified using a novel graphical model method for integrating and co-analyzing different data types in a network context. In general, this method can be used to infer direct associations between gene expression, methylation, SNP and clinical variables. Based on the results it was postulated that this SNP increases PARP1 activity, resulting in more efficient DNA repair, which helps cells recover from the treatment with alkylating agents, or alternatively decreases PARP1 trapping, which itself may account for a proportion of the cytotoxicity of alkylating agents. This finding was validated this finding by analyzing data on drug response, by inhibiting PARP1 activity in cell lines with and without the SNP and by looking for differential response to treatment with alkylating agents in combination with PARPi's.

By analyzing the TCGA RNA-seq melanoma data it was discovered that patients with one or two alleles of rs1805407 have increased relative abundance of isoform PARP1-003, which codes for a shortened PARP1 protein containing only the first zinc finger domain (exons 1 and 2) and no catalytic domain. Since this transcript seems to be caused by a mis-splicing of exons 2 and 3, it is safe to assume that the shorter form is caused by SNP rs1805405, the splice region variant 5 bp upstream of the beginning of exon 3. SNP rs1805405 is also in perfect LD with the focus of the present study, SNP rs1805407. Finally, Langelier et al. have shown that zinc finger-1 alone restores DNA-dependent PAR synthesis activity (Langelier M F, Planck J L, Roy S, & Pascal J M (2011) *J Biol Chem* 286(12):10690-1070). Thus, the short form of PARP1 could affect the activity of the full size PARP1 or decreases PARP1 trapping. Without being bound by theory, while the relative abundance of this isoform among the variants may not be substantial, it should be noted that the short isoform uniquely maintains the auto-modification domain, which is most critical to PARP trapping and this differential efficacy that was observed in the cells with variant SNP could be related to a differential effect on this domain by the SNP. It should be noted that while the difference in relative abundances of PARP1-001 and PARP1-003 appears very small in the TCGA data, those data are generated from pre-treatment samples. In tumors, PARP1 is an inducible enzyme whose expression is accelerated at the time of DNA damage. Without being bound by theory, the presence of SNP rs1805405 may affect the splicing rates and relative abundances of PARP1 isoforms, potentially by several-fold, and altering the relative protein levels of PARP1-001 and PARP1-003. This is relevant in patients especially knowing that TMZ is utilized in regimens that span either 5 days or 21 days out of 28-day cycles.

Without being bound by theory, is possible that SNP rs1805405 causes increased expression of the short form of PARP1 in patients with one or two variant alleles. This in turn increases the activity of PARP1 in trans, making it easier for cancer cells to escape treatment with DNA damage induced by alkylating agents. It also potentially abrogates the effect of PARP1 trapping in situ and therefore decreases the cyotoxicity of alkylating agents. Both effects would be significantly altered by PARP inhibition so that cells with the variant and increased expression of the short form will be experiencing increased PARP trapping upon PARP inhibition and therefore sustaining a much higher level of cell death than would be expected of alkylating agents alone resulting in the synergy that was observed even at relatively low doses of PARP inhibition. This implies that combination therapy with a PARPi may abrogate the observed resistance. This mechanism can also explain the observation that cells with the wild-type allele experience virtually no PARP1 trapping upon PARP inhibition and therefore combining PARPi's simultaneously with chemotherapy appears potentially antagonistic. Studies in cancer cell lines from various histologic subtypes indicated their relevance to the underlying biology of PARP inhibition; and are most remarkable in ovarian cancer for which the PARP inhibitor olaparib is FDA-approved.

Example 9

Materials and Methods

Melanoma study design: Using a retrospective cohort study design, 69 patients with metastatic melanoma who were treated with alkylator-based chemotherapy were evaluated. Frozen tissues were available from metastatic lesions on 21 patients and only pre-treatment tumor specimens were included in this analysis. In addition, formalin-fixed paraffin embedded tissues from 45 patients, for a total of 69 patients.

Chemotherapy regimens studied were primarily single-agent dacarbazine (DTIC), single-agent TMZ or DTIC-based combinations (including CVD, Cisplatin+Vinblastine+DTIC). Any other form of chemotherapy was excluded from the study. Response to chemotherapy was defined as documented objective tumor regression upon treatment. Patients were considered responders if their objective response was partial response or complete response after 2 or more cycles of chemotherapy or if they had stable disease on chemotherapy for longer than 4 months (to qualify for this designation patients had to have progressed within 2 months prior to initiation of chemotherapy). Patients with disease progression after 2 cycles of chemotherapy or with stable disease lasting less than 4 months were considered non-responders.

Gene Expression and methylation data collection: Total RNA was isolated from melanoma tissues using the PERFECTPURE™ RNA Tissue kit (5Prime Inc., MD, USA). RNA was quantified using RIBOGREEN™ RNA quantitation Kit (Molecular Probes, Eugene Oreg.) and its quality was evaluated by RNA Integrity Number using the Agilent BIOANALYZER™. Whole genome gene expression analysis was carried out using the ILLUMINA HT-12 Expression BEADCHIP™ (ILLUMINA, San Diego, Calif.) which targets more than 25,000 annotated genes with more than 48,000 probes derived from the REFSEQ (Build 36.2, Rel 22) and UNIGENE databases (Wheeler D L, et al. (2005) Database resources of the National Center for Biotechnology Information. *Nucleic Acids Res* 33 Database Issue:D39-45).

DNA was isolated from melanoma tissues using ARCHIVEPURE™ DNA Cell/Tissue kit (5Prime Inc., MD, USA). DNA samples (0.5 µg) were treated with sodium bisulphite using the EZ DNA METHYLATION GOLD™ kit (Zymo Research, Irvine, Calif.), and bisulphite-treated DNA was applied to an Illumina Infinium HUMANMETHYLATION27 BEADCHIP™ (Illumina, San Diego, Calif.) for DNA methylation profiling. This microarray permits the quantitative measurement of DNA methylation for 27,578 CpG dinucleotides spanning 14,495 genes. Methylation status of the interrogated CpG sites was determined by comparing β-values, the ratio of the fluorescent signal from the methylated allele to the sum from the fluorescent signals of both methylated and unmethylated alleles.

TAQMAN® Single Nucleotide Polymorphism (SNP) Genotyping Assay: Genomic DNA was extracted from the full panel of cancer cell lines using QIAAMP DNA MINI™ kit (Qiagen, Calencia, Calif.) and subjected to SNP Genotyping using a TAQMAN® SNP Genotyping assay (C_11639200_20, SNP ID: rs1805407) (Applied BIOSYSTEMS™, Waltham, Mass.). Each reaction contained 12.5 µL TAQMAN® Universal PCR Master Mix, 0.625 µL TAQMAN® SNP Genotyping Assay, 10.875 µL distilled water and 1 µL gDNA (10 ng/µL), with a final reaction volume of 25 µL. Positive control samples for the three possible genotypes were included with each genotyping reaction. In addition, at least two no template controls were included.

Cell lines: A panel of human tumor cell lines representative of five common cancers were used: melanoma (FEMX, A375, M14, MW-852, WM-115, SK-Mel-31 and SK-Mel-2), colon (HT-29, LoVo, SW620, HCT-116 and LS174T), breast (MCF-7 and MDA-MB-231), ovarian (SKOV-3 and A2780) and lung (A549, Calu-6, H-460 and H522). HT-29, HCT-116, H-522, LoVo, SW620, MDA-MB-231, MCF-7, SKOV-3, H460, A549, Calu-6, LS174T, M14, FEMX, A2780, SK-Mel-2, WM-115, A375, WM-852 and SK-MEL-31. All cell lines were cultured according to their recommendations (in RPMI-1640 or DMEM medium supplemented with 10% FBS) without antibiotics and routinely tested for *Mycoplasma*. Cell lines were grown in monolayer at 37° C. in a humidified atmosphere containing 5% CO2 and routinely sub-cultured twice weekly.

PARP1 cell proliferation and drug interaction assays: RPMI 1640 and Dulbecco's modified Eagle medium (DMEM) with L-Glutamine, cell culture media were purchased from Cellgro (Mediatech, Inc.). Heat-inactivated Foundation Fetal bovine serum (FBS) was purchased from Gemini bio-products. The alkylating agent, methyl methanesulfonate (MMS) was purchased from Sigma. The PARPi veliparib (ABT-888, Abbott Laboratories, Abbott Park, Ill., USA) was used in the cell proliferation assays. The ABT-888 used in the drug interaction assays was purchased from Selleck Chemicals LLC (Huston, Tex., USA). MMS is an alkylating agent that results in DNA damage at the same bases as dacarbazine and temozolomide and has been used extensively as an alternative in the laboratory setting. ABT-888 was dissolved in dimethyl sulfoxide (DMSO) to a stock solution of 10 mM. A 10 μM working solution was then prepared in PBS for subsequent serial dilutions. The final concentration of DMSO in drug-treated cultures (MTT assays) was always less than 0.5% (v/v) and did not contribute to cytotoxicity (data not shown).

The cytotoxic effect of the PARP inhibitor veliparib (ABT-888) and the alkylating agent, MMS was assessed using the MTT colorimetric dye reduction assay, according to the manufacturer's instructions (TACS® MTT Cell Proliferation Assay (MTT-CPA) from Trevigen, Inc.). MTT assay was used for each cell line to determine the half-maximal (50%) inhibitory concentration ($IC_{50}$) values of MMS alone or in combination with ABT-888. Briefly, cells were seeded in triplicates in 96 wells at appropriate cell density (optimized for each individual cell line to have exponentially growing cells during the course of the assay), in their regular culture medium (DMEM with L-Glutamine from Cellgro (Mediatech, Inc.)). After 24 h, the medium was aspirated and the cells were incubated with increasing concentrations of MMS alone (0 to 1 mM) or in the presence of a fixed concentration (10 nM final) of ABT-888 (six replicates for each combination treatment) for 72 h at 37° C. Then, 10 μl of MTT Reagent was added to each well and the plates were incubated for another 4 h at 37° C. in the dark. In each well, 100 μl of Detergent Reagent was then added and incubated at 37° C. until complete solubilization of formazan crystals.

In single drug treatment experiments (MMS alone), drug-free controls containing 0.5% DMSO were included. In drug combination experiments with increasing concentrations of MMS, the samples with PARPi alone (fixed concentration of 10 nM of ABT-888), were used as controls. All control values were normalized to 100%. Cell viability was measured by reading the absorbance at 570 nm using a Tecan (Safire 2) microplate reader. Reading was converted to the percentage of the controls. The values obtained for each of the triplicates were averaged, and $IC_{50}$ values were defined as the concentrations of drug(s) that inhibited growth by 50% relative to controls. The data from the MTT assay were expressed as mean $IC_{50}$±standard deviation (SD). The $IC_{50}$ of ABT-888, MMS and linear regression analysis were computed by GRAPHPAD Prism 5.0 program (GRAPHPAD Software, Inc., San Diego, Calif.). For each cell line, the P-value was calculated using the Student t-test (two-tailed, paired) to compare the $IC_{50}$ means of each treatment group (MMS alone or MMS+ABT-888).

For drug combinations, similar experiments were performed except that in each 96-well plate, cells were exposed to medium alone (DMSO controls), single drugs alone (ABT-888 only or MMS only) or to different concentrations of the two drugs combined at the constant molar ratio of their $IC_{50}$ values in each specific cell line. ABT-888 $IC_{50}$ value was determined for each individual cell line using GRAPHPAD Prism Software as previously described.

The possible interaction between ABT-888 and MMS was investigated by the Chou and Talalay median effect principle using the Compusyn Software (version 1.0, ComboSyn Inc.; Paramus, N.J., USA). The program calculates a combination index (C.I.) that is used to identify synergistic, additive, and antagonistic drug interactions. The type of interaction is determined by plotting C.I. versus the fraction of cells affected (Fa) by increasing drug concentrations, where the drugs are added at the molar ratio of their specific $IC_{50}$ values in each cell line. Five dilutions ranging from one fourth of the $IC_{50}$ to four times the $IC_{50}$ (serial dilution factor=2) of each drug in combination plus a control was tested in three independent experiments with duplicate samples.

Dose-effect curve parameters, C.I. values, Fa-CI plot (plot representing C.I. versus Fa, the fraction affected by a particular dose) were calculated by Compusyn Program (Compusyn Inc., Paramus, N.J., USA). C.I. values of three independent experiments were used for calculation of the mean values±standard deviation (SD). A one-tailed Student's t test with significance level of $p<0.05$ was used to evaluate whether C.I. values were lower (synergy) or higher than 1 (antagonism). A C.I.=1 represents mere additive effects.

Computational analysis methods: The MGM-Learn platform was developed in MATLAB and is available upon request. Undirected graphs are learned using the MATLAB code from stanford.edu/jd117/learningmgm_html. For the non-paranormal normalization HUGE (Zhao T, Liu H, Roeder K, Lafferty J, & Wasserman L (2012) *The Journal of Machine Learning Research* 98888:1059-1062) was used. To quantify PARP1 isoform abundances from paired-end reads of TCGA metastatic melanoma samples we used kallisto (Bray N, Pimentel H, Melsted P, & Pachter L (2015) *arXiv preprint arXiv*:1505.02710) using transcript definitions from Ensembl (Flicek P, et al. (2013) Ensembl 2014. *Nucleic acids research*:gkt1196).

SNP imputation on TCGA samples and NCI-60 cell lines: NCI-60 data were obtained from Cell Miner in June 2013 (discover.nci_nih.gov/cellminer/). For those cell lines or TCGA samples for which the identity of SNP rs1805407 was not available we used imputation to infer its identity. Using SNAP (17) we found 51 SNPs to be in perfect linkage disequilibrium (LD) with rs1805407 ($R^2=1$). Of these, 9 variants were covered by the Affymetrix SNP Array 6.0 used by the TCGA. To determine the rs1805407 genotype in TCGA samples birdseed calls (Korn J M, et al. (2008) *Nature genetics* 40(10):1253-126) from Affymetrix Genome-Wide Human SNP Array 6.0 were used. Only samples with a birdseed confidence less than 0.1 or where all 9 SNPs in perfect LD agreed with the birdseed call were used.

Example 10

Detailed Description of the MGM-Learn Algorithm

The MGM-Learn (Mixed Graphical Model Learning) algorithm is a modular computational framework to learn a causal or partially causal graph structure over mixed data types, namely continuous and discrete variables. It consists of four steps.

Filtering step. If the dataset contains omics data with thousands to millions of variables a filtering step is needed to select those variables that are more likely to be relevant to the clinical problem. Possible methods for this filtering step include a variance filter, using prior knowledge to select genes or pathways that are likely to be involved in the disease of interest, or using a statistical filter to choose genes that are highly correlated with or predictive of certain disease features. A generalized correlation measure (described below) wase used that is able to calculate correlation between pairs of variables that can be categorical or continuous. The 1000 features most correlated with response to treatment were selected using this measure.

Normalization step. Most methods that identify conditional dependencies between continuous variables require these variables to be normally distributed. This is not the case with some of the biomedical data. For example, RNA-seq data are distributed according to the negative binomial distribution (Anders S & Huber W (2010) *Genome Biol* 11(10):R106). The continuous variables were normalized using the non-paranormal transformation (Liu H, Lafferty J, & Wasserman L (2009) *The Journal of Machine Learning Research* 10:2295-232). This method maps each data feature to a normal distribution which helps to satisfy the assumptions of normality in our subsequent methods and to allow us to learn a network over differently distributed data sources (Puniyani K & Xing E P (2013) *Journal of computational biology: a journal of computational molecular cell biology* 20(11):892-90).

Learning undirected graph over mixed type variables. The likelihood of a mixed graphical model (MGM) can be described as follows (Lee J & Hastie T (2013) *Journal of Machine Learning Research* 31:388-39):

$$p(x, y, \Theta) \propto \exp\left(\sum_{s=1}^{p} \sum_{t=1}^{p} -\frac{1}{2}\beta_{st}x_s x_t + \sum_{s=1}^{p} \alpha_s x_s + \sum_{s=1}^{p} \sum_{j=1}^{q} \rho_{sj}(y_j)x_s + \sum_{j=1}^{q} \sum_{r=1}^{q} \varphi_{rj}(y_r, y_j)\right)$$

where $\beta$ is the edge potential between each pair of continuous features, $\alpha$ is the node potential of a continuous feature, $\rho$ is the edge potential between continuous and discrete features and $\varphi$ is the edge potential between pairs of discrete features. Since computing the exact likelihood for this mixed model is computationally intractable, the use of the pseudolikelihood (Besag J (1975) *J R Stat Soc D* 24(3):179-195) is necessary. For this step we used the Lee and Hastie pseudolikelihood calculation (Lee J & Hastie T (2013) *Journal of Machine Learning Research* 31:388-39):

$$\tilde{l}(\Theta \mid x, y) = -\sum_{s=1}^{p} \log p(x_s \mid x_{\backslash s}, y; \Theta) - \sum_{r=1}^{q} \log p(y_r \mid x, y_{\backslash r}; \Theta)$$

where $$-\sum_{s=1}^{p} \log p(x_s \mid x_{\backslash s}, y; \Theta) = -\frac{1}{2}\left(\log \beta_{ss} + \beta_{ss}\left(\sum_{j}\frac{\rho_{sj}(y_j)}{\beta_{ss}} - \sum_{t \neq s}\frac{\beta_{st}}{\beta_{ss}}x_t - x_s\right)^2\right)$$

and $$-\sum_{r=1}^{q} \log p(y_r \mid x, y_{\backslash r}; \Theta) = -\log \frac{\exp\left(\sum_s \rho_{sr}(y_r)x_s + \varphi_{rr}(y_r, y_r) + \sum_{j \neq r}\varphi_{rj}(y_r, y_j)\right)}{\sum_{l=1}^{L_r} \exp\left(\sum_s \rho_{sr}(l)x_s + \varphi_{rr}(l, l) + \sum_{j \neq r}\varphi_{rj}(l, y_j)\right)}$$

This pseudolikelihood is convex and efficiently computable. Learning is performed using accelerated proximal gradient methods implemented in TFOCS (52). We used Nesterov's 1983 method for optimization with a maximum of 700 iterations for our stability runs and 1000 iterations for all other runs. The Stability Approach was used to Regularization Selection (StARS) method (Becker S R, Candès E J, & Grant M C (2011) *Math. Prog. Comp.* 3(3):165-218) on the range $0.1 < \lambda < 0.3$ subject to an instability threshold of 0.05 to select the value $\lambda = 0.2$ which was used to learn the model presented in the results.

Causal filtering step. Undirected graphs learned over datasets produced by an underlying directed model tend to generate false positive edges. Indeed, when there is a "collider" in the true graph, $X \rightarrow Z \leftarrow Y$ (i.e., X and Y are causing Z) then the learned undirected model will be X-Z-Y-X. This is because X and Y are dependent given Z or Dep(X, Y|Z). The false positive edge X-Y can be removed if a conditional independence test is performed over all possible subsets. For example, in the simple case of $X \rightarrow Z \leftarrow Y$, it is found that Ind(X, Y|∅), and so the X-Y edge will be removed and correct orientation of the $X \rightarrow Z$ and $Z \leftarrow Y$ edges will be thus established. In addition for some additional undirected edge, Z-W, in the absence of the edges X-W and Y-W, the direction $Z \rightarrow W$ is inferred. This is because a $Z \leftarrow W$ true edge would have produced false positive edges X-W and Y-W. This is called the causal filtering step. Algorithmically the procedure is followed for PC-Stable (Colombo D & Maathuis M H (2014) *The Journal of Machine Learning Research* 15(1):3741-378) except it starts from the MGM graph rather than a fully connected graph, and since acyclicity is not assumed, and only orientation rule R1 is used.

Generalized Correlation. In order to measure association between a continuous and categorical variable or two categorical variables the following strategy is used. It is desirous to calculate the equivalent of Pearson's product moment coefficient for each possible pairing of these variables. The general formula for Pearson's correlation between two vectors of observations, X and Y, with means $\mu_X$ and $\mu_Y$ and standard deviations $\sigma_X$ and $\sigma_Y$ is $$r_{XY} = \frac{\text{cov}(X, Y)}{\sigma_X \sigma_Y}$$

where covariance is defined as $\text{cov}(X, Y) = E[(X-\mu_X)(Y-\mu_Y)]$. This is a standard calculation for pairs of continuous variables because mean and standard deviation are well defined. For pairs of binary variables, these values are also well defined, and this formulation is called the Matthews' Correlation Coefficient. For categorical variables the covariance can be calculated on a category by category basis. So for a categorical X continuous Y, it can be focused on a, one of the categories of X when calculating a sample covariance:

$$\text{cov}(X_a, Y) = E[(X_a - \mu_{X_a})(Y - \mu_Y)] = \frac{1}{N-1}\sum_{i=1}^{N}[(\mathbb{I}(X_i = a) - \hat{p}_a)(Y_i - \hat{\mu}_Y)]$$

where $\mathbb{I}(X_i=a)$ is an indicator function that is 1 when $X_i=a$ and zero otherwise, and $$\hat{p}_a = \frac{1}{N}\sum_{i=1}^{N} \mathbb{I}(X_i = a)$$

or the empirical probability of observing a in X. Since $\mathbb{I}(X_i=a)$ is equivalent to a Bernoulli random variable now it is easy to see that the sample standard deviation is $$\hat{\sigma}_{X_a} = \sqrt{\frac{N}{N-1}\hat{p}_a(1-\hat{p}_a)}.$$

Similarly, if both X and Y are categorical, look at each possible pairing of categories separately so $$\text{cov}(X_a, Y_b) = \frac{1}{N-1}\sum_{i=1}^{N}[(\mathbb{1}(X_i = a) - \hat{p}_a)(\mathbb{1}(Y_i = b) - \hat{q}_b)]$$

where $\hat{q}_b$ is the empirical probability of observing b in Y. So, in a discrete-continuous pair, we now have a vector for the covariance and a vector for the standard deviations corresponding to the different levels of the categorical variable, we use the $l_2$ norm to calculate a single score from these vectors (where X is categorical):

$$r_{XY} = \frac{\|\text{cov}(X, Y)\|_2}{\|\sigma_X\|\sigma_Y}.$$

In the discrete-discrete case we have two matrices corresponding to the possible pairs of levels in the two variables, and we combine them with the Frobenius norm:

$$r_{XY} = \frac{\|\text{cov}(X, Y)\|_F}{\|\sigma_X\sigma_Y\|_F}.$$

Both of these cases result in non-negative values so to make the continuous-continuous values comparable with the others we take the absolute value so scores for all pairs of edges fall on the interval [0,1].

One motivation for this approach is that these sample covariances turn out to be proportional to the partial gradients of negative log pseudolikelihood in a factorized (i.e. zero edges) MGM as described above with respect to the edge parameters and variable levels (see (5) supplement). Namely:

$$\frac{\partial \tilde{l}}{\partial \beta_{ij}} = -2*(N-1)*\text{cov}(X, Y), \frac{\partial \tilde{l}}{\partial \rho_{ij}(a)} = -2*(N-1)*\text{cov}(X_a, Y)$$

$$\text{and } \frac{\partial \tilde{l}}{\partial \phi_{ij}(a,b)} = -2*(N-1)*\text{cov}(X_a, Y_b)$$

where X is the indexed by i and Y is indexed by j in the MGM and the pairs of X and Y are continuous-continuous, discrete-continuous, and discrete-discrete respectively.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

We claim:

1. A method for treating a human subject with cancer, comprising:
   a) obtaining a biological sample from the human subject with cancer;
   b) detecting the presence of a single nucleotide polymorphism in the biological sample, wherein the single nucleotide polymorphism is a C at rs1805407;
   c) diagnosing the human subject as having a cancer sensitive to treatment with a PARP1 inhibitor in combination with a second chemotherapeutic agent, wherein the second chemotherapeutic agent is an alkylating agent or a DNA damaging agent; and
   d) administering the PARP1 inhibitor and the second chemotherapeutic agent to the diagnosed human subject.

2. A method for treating a subject with cancer, comprising:
   a) detecting the presence of a C at rs1805407 in a biological sample from the subject with cancer;
   c) diagnosing the subject as having a cancer sensitive to treatment with a PARP1 inhibitor in combination with a second chemotherapeutic agent, wherein the second chemotherapeutic agent is an alkylating agent or a DNA damaging agent; and
   d) administering the PARP1 inhibitor and the second chemotherapeutic agent to the diagnosed subject.

3. The method of claim 1, wherein the alkylating agent is temozolomide, carmustine, cyclophosphamide or parthenolide.

4. The method of claim 1 wherein the PARP1 inhibitor is veliparib (ABT-888), olaparib, nirparib, BMN 673, rucaparib, CDP-9722, or E7016.

5. The method of claim 1, wherein the second chemotherapeutic agent is the DNA damaging agent.

6. The method of claim 5, wherein the second chemotherapeutic agent is temozolomide, methanesulfonate, dacarbazine, cisplatin, carboplatin, oxaliplatin, gemcitabine, 5-Fluorouracil, cytarabine, doxorubicin, idarubicin, or epirubicin.

7. The method of claim 1, wherein the cancer is a melanoma, an ovarian cancer, a lung cancer, a colon cancer or a breast cancer.

8. The method of claim 1, wherein the cancer is a melanoma.

9. The method of claim 1, wherein detecting the presence of the C at rs1805407 comprises the use of an array or a polymerase chain reaction.

10. The method of claim 9, wherein performing PCR comprises
    amplifying genomic DNA from a biological sample to form amplified synthetic DNA; and
    detecting the C at rs1805407 in the amplified synthetic DNA.

11. A method of treating a cancer in a subject, comprising detecting the presence of a C at rs1805407 PARP1 gene in a biological sample from the subject, wherein the biological sample comprises genomic DNA, and wherein detection of a C at rs1805407 in the PARP1 gene indicates the subject is sensitive to treatment with the PARP1 inhibitor and an alkylating agent; and
    administering the PARP1 inhibitor and the alkylating agent to the subject, wherein the PARP1 inhibitor is veliparib (ABT-888), olaparib, nirparib, BMN 673, rucaparib, CDP-9722, or E7016, and wherein the alkylating agent is temozolomide, methanesulfonate, carmustine, cyclophosphamide or parthenolide, thereby treating the cancer.

12. The method of claim 11, wherein the PARP1 inhibitor is veliparib (ABT-888).

13. The method of claim 11, wherein the alkylating agent is temozolomide.

14. The method of claim 11, wherein the cancer is a melanoma, an ovarian cancer, a lung cancer, a colon cancer or a breast cancer.

15. The method of claim 14, wherein the cancer is a melanoma.

16. The method of claim 11, further comprising
    isolating genomic DNA from the biological sample; and
    performing polymerase chain reaction to amplify DNA comprising a C at rs1805407 in the PARP1 gene.

17. The method of claim 11, wherein the alkylating agent is temozolomide and wherein the PARP1 inhibitor is veliparib (ABT-888).

* * * * *

SEQUENCE LISTING

<160> NUMBER OF SEQ ID NOS: 4

<210> SEQ ID NO 1
<211> LENGTH: 51
<212> TYPE: DNA
<213> ORGANISM: Homo sapiens

<400> SEQUENCE: 1
tgggagaggg caagctgggg gaggtttgct ttgctctctg agacgaggcc c        51

<210> SEQ ID NO 2
<211> LENGTH: 51
<212> TYPE: DNA
<213> ORGANISM: Homo sapiens

<400> SEQUENCE: 2
tgggagaggg caagctgggg gaggtctgct ttgctctctg agacgaggcc c        51

<210> SEQ ID NO 3
<211> LENGTH: 51
<212> TYPE: DNA
<213> ORGANISM: Homo sapiens

<400> SEQUENCE: 3
accctctccc gttcgacccc ctccaaacga aacgagagac tctgctccgg g        51

<210> SEQ ID NO 4
<211> LENGTH: 51
<212> TYPE: DNA
<213> ORGANISM: Homo sapiens

```
<400> SEQUENCE: 4
accctctccc gttcgacccc ctccagacga aacgagagac tctgctccgg g        51
```